(12) United States Patent
Davis et al.

(10) Patent No.: US 10,206,429 B2
(45) Date of Patent: Feb. 19, 2019

(54) AEROSOL DELIVERY DEVICE WITH RADIANT HEATING

(71) Applicant: R.J. Reynolds Tobacco Company, Winston-Salem, NC (US)

(72) Inventors: Michael F. Davis, Clemmons, NC (US); Yi-ping Chang, Greensboro, NC (US); Stephen Benson Sears, Siler City, NC (US); Karen V. Taluskie, Winston-Salem, NC (US); Susan K. Pike, Pilot Mountain, NC (US); Nicholas Harrison Watson, Westfield, NC (US); Stephen C. Reynolds, Dobson, NC (US)

(73) Assignee: RAI Strategic Holdings, Inc., Winston-Salem, NC (US)

(*) Notice: Subject to any disclaimer, the term of this patent is extended or adjusted under 35 U.S.C. 154(b) by 370 days.

(21) Appl. No.: 14/958,651

(22) Filed: Dec. 3, 2015

(65) Prior Publication Data

US 2017/0020193 A1    Jan. 26, 2017

Related U.S. Application Data

(63) Continuation-in-part of application No. 14/808,450, filed on Jul. 24, 2015.

(51) Int. Cl.
*F24F 6/08* (2006.01)
*A24F 47/00* (2006.01)
(Continued)

(52) U.S. Cl.
CPC ......... *A24F 47/008* (2013.01); *A61M 11/041* (2013.01); *A61M 11/042* (2014.02); *A61M 15/06* (2013.01); *H05B 3/04* (2013.01); *H05B 3/145* (2013.01); *H05B 3/44* (2013.01); *A61M 2016/0021* (2013.01); *A61M 2205/368* (2013.01); *A61M 2205/3653* (2013.01);
(Continued)

(58) Field of Classification Search
None
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

*Primary Examiner* — Thor Campbell
(74) *Attorney, Agent, or Firm* — Womble Bond Dickinson (US) LLP

(57) ABSTRACT

The present disclosure relates to aerosol delivery devices, methods of forming such devices, and elements of such devices. In some embodiments, the present disclosure provides devices configured for vaporization of an aerosol precursor composition through radiant heating. The radiant heat source may be a laser diode or further element suitable for providing electromagnetic radiation, and heating may be carried out within an optional chamber, which can be a radiation-trapping chamber. In some embodiments, an interior of such chamber may be configured as a black body or as a white body.

23 Claims, 15 Drawing Sheets

(51) Int. Cl.
*A61M 11/04* (2006.01)
*A61M 15/06* (2006.01)
*H05B 3/04* (2006.01)
*H05B 3/14* (2006.01)
*H05B 3/44* (2006.01)
*A61M 16/00* (2006.01)

(52) U.S. Cl.
CPC ............. *A61M 2205/8206* (2013.01); *H05B 2203/014* (2013.01); *H05B 2203/018* (2013.01); *H05B 2203/019* (2013.01); *H05B 2203/02* (2013.01); *H05B 2203/021* (2013.01); *H05B 2203/022* (2013.01); *H05B 2203/032* (2013.01)

(56) References Cited

U.S. PATENT DOCUMENTS

| | | | |
|---|---|---|---|
| 2,104,266 A | 1/1938 | McCormick | |
| 3,200,819 A | 8/1965 | Gilbert | |
| 3,651,240 A * | 3/1972 | Kirkpatrick | F27D 11/02 118/715 |
| 4,284,089 A | 8/1981 | Ray | |
| 4,303,083 A | 12/1981 | Burruss, Jr. | |
| 4,640,233 A * | 2/1987 | Draper | F22B 35/004 122/1 C |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,154,192 A | 10/1992 | Sprinkel et al. | |
| 5,249,586 A | 10/1993 | Morgan et al. | |
| 5,261,424 A | 11/1993 | Sprinkel, Jr. | |
| 5,264,681 A * | 11/1993 | Nozaki | F23Q 7/22 219/270 |
| 5,322,075 A | 6/1994 | Deevi et al. | |
| 5,353,813 A | 10/1994 | Deevi et al. | |
| 5,369,723 A * | 11/1994 | Counts | A24F 47/008 128/202.21 |
| 5,372,148 A | 12/1994 | McCafferty et al. | |
| 5,388,574 A | 2/1995 | Ingebrethsen et al. | |
| 5,408,574 A | 4/1995 | Deevi et al. | |
| 5,468,936 A | 11/1995 | Deevi et al. | |
| 5,498,850 A | 3/1996 | Das | |
| 5,515,842 A | 5/1996 | Ramseyer et al. | |
| 5,530,225 A | 6/1996 | Hajaligol | |
| 5,564,442 A | 10/1996 | MacDonald et al. | |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiling et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,164,287 A | 12/2000 | White | |
| 6,196,218 B1 | 3/2001 | Voges | |
| 6,196,219 B1 | 3/2001 | Hess et al. | |
| 6,580,875 B2 * | 6/2003 | Rymer | A01M 1/2077 392/392 |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,854,461 B2 | 2/2005 | Nichols | |
| 6,854,470 B1 | 2/2005 | Pu | |
| 7,040,314 B2 | 5/2006 | Nguyen et al. | |
| 7,117,867 B2 | 10/2006 | Cox et al. | |
| 7,217,320 B2 | 5/2007 | Kim et al. | |
| 7,293,565 B2 | 11/2007 | Griffin et al. | |
| 7,513,253 B2 | 4/2009 | Kobayashi et al. | |
| 7,726,320 B2 | 6/2010 | Robinson et al. | |
| 7,775,459 B2 | 8/2010 | Martens, III et al. | |
| 7,832,410 B2 | 11/2010 | Hon | |
| 7,845,359 B2 | 12/2010 | Montaser | |
| 7,896,006 B2 | 3/2011 | Hamano et al. | |
| 8,127,772 B2 | 3/2012 | Montaser | |
| 8,190,006 B2 * | 5/2012 | Wendt | C23C 14/0021 392/388 |
| 8,205,622 B2 | 6/2012 | Pan | |
| 8,314,591 B2 | 11/2012 | Terry et al. | |
| 8,365,742 B2 | 2/2013 | Hon | |
| 8,402,976 B2 | 3/2013 | Fernando et al. | |
| RE44,312 E * | 6/2013 | Vieira | A01M 1/2077 219/486 |
| 8,499,766 B1 | 8/2013 | Newton | |
| 8,528,569 B1 | 9/2013 | Newton | |
| 8,539,959 B1 | 9/2013 | Scatterday | |
| 8,550,069 B2 | 10/2013 | Alelov | |
| 8,873,941 B2 * | 10/2014 | Row | A61M 16/1075 219/544 |
| 8,910,640 B2 | 12/2014 | Sears et al. | |
| 9,744,320 B2 * | 8/2017 | Wakalopulos | A61M 15/06 |
| 2002/0078946 A1 | 6/2002 | Sprinkel, Jr. et al. | |
| 2002/0146242 A1 | 10/2002 | Vieira | |
| 2002/0181946 A1 * | 12/2002 | Brown | A01M 1/2077 392/390 |
| 2003/0007787 A1 * | 1/2003 | Rymer | A01M 1/2077 392/395 |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0170405 A1 | 9/2004 | Sherwood et al. | |
| 2004/0200488 A1 | 10/2004 | Felter et al. | |
| 2004/0226568 A1 | 11/2004 | Takeuchi et al. | |
| 2005/0016550 A1 | 1/2005 | Katase | |
| 2005/0126562 A1 | 6/2005 | Rabinowitz et al. | |
| 2006/0016453 A1 | 1/2006 | Kim | |
| 2006/0196518 A1 | 9/2006 | Hon | |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2009/0283103 A1 | 11/2009 | Nielsen et al. | |
| 2009/0320863 A1 | 12/2009 | Fernando et al. | |
| 2010/0031968 A1 | 2/2010 | Sheikh et al. | |
| 2010/0043809 A1 | 2/2010 | Magnon | |
| 2010/0083959 A1 | 4/2010 | Siller | |
| 2010/0163063 A1 | 7/2010 | Fernando et al. | |

(56) References Cited

U.S. PATENT DOCUMENTS

| | | |
|---|---|---|
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1* | 6/2011 | Thorens ............... H05B 3/58 131/329 |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0008457 A1 | 1/2013 | Zheng et al. |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0180553 A1 | 7/2013 | Kim et al. |
| 2013/0192619 A1 | 8/2013 | Tucker et al. |
| 2013/0192623 A1 | 8/2013 | Tucker et al. |
| 2013/0213417 A1 | 8/2013 | Chong et al. |
| 2013/0255702 A1 | 10/2013 | Griffith, Jr. et al. |
| 2013/0298905 A1 | 11/2013 | Leven et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0059780 A1 | 3/2014 | Lafleche et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak, III et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0305454 A1* | 10/2014 | Rinker ............... A24F 47/008 131/329 |
| 2014/0334802 A1* | 11/2014 | Dubief ............... A61L 9/03 392/390 |
| 2014/0345631 A1 | 11/2014 | Bowen et al. |
| 2015/0020823 A1 | 1/2015 | Lipowicz et al. |
| 2015/0020830 A1 | 1/2015 | Koller |
| 2015/0053217 A1 | 2/2015 | Steingraber et al. |
| 2015/0068541 A1* | 3/2015 | Sears ............... A24F 47/008 131/328 |
| 2015/0078735 A1* | 3/2015 | Cormack ............... A61M 15/06 392/395 |
| 2015/0090279 A1 | 4/2015 | Chen |
| 2015/0136158 A1 | 5/2015 | Stevens et al. |
| 2015/0164147 A1 | 6/2015 | Verleur et al. |
| 2015/0305409 A1* | 10/2015 | Verleur ............... H02J 7/0022 131/329 |
| 2015/0320116 A1* | 11/2015 | Bleloch ............... A61M 15/06 219/628 |
| 2015/0351456 A1 | 12/2015 | Johnson et al. |
| 2016/0044962 A1* | 2/2016 | Thorens ............... A24F 47/008 392/395 |
| 2016/0089508 A1* | 3/2016 | Smith ............... A61M 15/06 128/200.16 |
| 2016/0120229 A1* | 5/2016 | Tucker ............... H01C 17/00 131/329 |
| 2016/0135505 A1 | 5/2016 | Li et al. |
| 2017/0303586 A1* | 10/2017 | Sur ............... A24F 47/008 |
| 2017/0303592 A1* | 10/2017 | Cameron ............... A24F 47/008 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 203646497 | 6/2014 |
| CN | 104522892 | 4/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2014/182736 | 11/2014 |

* cited by examiner

AEROSOL DELIVERY DEVICE WITH RADIANT HEATING

CROSS-REFERENCE TO RELATED APPLICATIONS

The present application is a continuation-in-part of U.S. patent application Ser. No. 14/808,450, filed Jul. 24, 2015, the disclosure of which is incorporated herein by reference.

FIELD OF THE DISCLOSURE

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference. See also, for example, the various types of smoking articles, aerosol delivery devices, and electrically powered heat generating sources referenced by brand name and commercial source in U.S. patent application Ser. No. 14/170,838 to Bless et al., filed Feb. 3, 2014, which is incorporated herein by reference in its entirety.

It would be desirable to provide a reservoir for an aerosol precursor composition for use in an aerosol delivery device, the reservoir being provided so as to improve formation of the aerosol delivery device. It would also be desirable to provide aerosol delivery devices that are prepared utilizing such reservoirs.

SUMMARY OF THE DISCLOSURE

The present disclosure relates to aerosol delivery devices, methods of forming such devices, and elements of such devices. The aerosol delivery devices can provide for improved heating of aerosol precursor compositions through utilization of radiant heating and/or through utilization of focused heating. Configurations of aerosol delivery devices that utilize radiant heating can be particularly beneficial in that there can be little to no charring of a wick that is being heated to vaporize a liquid transported thereby. Use of radiant heating also can significantly increase the usable lifetime of a heater and/or wick in an aerosol delivery device. Furthermore, radiant heating can be beneficial in reducing and/or eliminating any thermal degradation components formed by heating of an aerosol precursor liquid. Radiant heating likewise can mitigate or eliminate problems in known aerosol forming devices, such as pyrolysis and/or deposition of char at the interface between a wick and a heating wire wrapped around the wick.

In some embodiments, the devices can include a chamber that is configured for trapping electromagnetic radiation that may be delivered therein. The chamber may provide for trapping of the radiation at least in part due to the configuration of an interior surface of a wall of the chamber. In some embodiments, the devices can include a heater that provides focused heating, such as a laser diode. Preferably, a laser diode can be configured to deliver electromagnetic radiation at a specific wavelength or band of wavelengths that can be tuned for vaporization of the aerosol precursor composition and/or tuned for heating a wick or similar element via which the aerosol precursor composition may be provided for vaporization. The laser diode can particularly be positioned so as to deliver the electromagnetic radiation within a chamber, and the chamber may be configured to be radiation-trapping. Although laser diodes may be preferred, other heat sources, including resistive heating wires, microheaters, or the like, may be utilized. Suitable microheaters are described in U.S. Pat. No. 8,881,737 to Collett et al., which is incorporated herein by reference. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The combination of a chamber and a heater, such as a laser diode, may form an atomizer, and the atomizer also may include a wick or like element. The atomizer may be positioned within an outer shell, which may define the aerosol delivery device. Such outer shell may include all elements necessary for forming the aerosol delivery device. In some embodiments, the outer shell may be combined with a control body, which itself may include a housing that includes elements, such as a power source, a microcontroller, a sensor, and an output (e.g., a light emitting diode (LED), haptic feedback element, or the like).

In some embodiments, an aerosol delivery device according to the present disclosure can comprise an outer shell, a radiation-trapping chamber positioned within the outer shell and comprising a chamber wall, and a radiation source configured to provide radiation within the radiation-trapping chamber. The aerosol delivery device may be defined by one or more further characteristics, the following statements being exemplary thereof and being combinable in any manner.

The radiation-trapping chamber in the aerosol delivery device can be substantially spherical.

The radiation-trapping chamber in the aerosol delivery device can be substantially elongated (e.g., substantially tubular).

An interior of the radiation-trapping chamber (e.g., an interior surface of the wall forming the chamber or a surface of a wall within the chamber) can be configured to one or more of absorb, emit, and reflect radiation from the radiation source.

The interior of the radiation-trapping chamber can be configured as a black body.

The interior of the radiation-trapping chamber can be configured as a white body.

The radiation-trapping chamber can comprise an inlet and an outlet in fluid communication.

The radiation source can be positioned on the chamber wall of the radiation-trapping chamber.

The radiation source can be positioned within the radiation-trapping chamber and spaced apart from the chamber wall.

The radiation source can extend substantially along a longitudinal axis of the aerosol delivery device, particularly so as to be substantially parallel with the longitudinal axis.

The radiation source can comprise a laser diode.

The radiation source can be configured to emit electromagnetic radiation with a wavelength in the range of about 390 nm to about 1 mm.

The radiation source can be configured to emit electromagnetic radiation with a wavelength in the range of visible light.

The radiation source can be configured to emit electromagnetic radiation with a wavelength in the range of violet light to far infrared light.

The radiation source can be configured to emit electromagnetic radiation within a wavelength band having a bandwidth that is no greater than 1,000 nm, that is no greater than 500 nm, that is no greater than 250 nm, that is no greater than 100 nm, that is no greater than 50 nm, that is no greater than 10 nm, that is no greater than 5 nm, or that is no greater than 2 nm.

The aerosol delivery device can comprise a wick configured to deliver an aerosol precursor composition within the radiation-trapping chamber.

The wick can pass through at least one aperture in the chamber wall of the radiation-trapping chamber such that a first section of the wick is positioned exterior to the radiation-trapping chamber and a second section of the wick is positioned interior to the radiation-trapping chamber. The second section of the wick can be a vaporization section, and the first section of the wick can be a transport section. The first section of the wick may define arms that extend away from the second section of the wick.

The radiation source can be in contact with at least a portion of the second section of the wick.

The second section of the wick can be positioned substantially perpendicular to a longitudinal axis of the outer shell.

The wick can be configured as a layer lining at least a portion of an interior of the chamber wall of the radiation-trapping chamber.

The chamber wall of the radiation-trapping chamber can comprise a channel extending therethrough, and a portion of the wick can be extending through the channel.

The outer shell can comprise an air entry and can comprise a mouthend with an aerosol port.

The aerosol delivery device can comprise an air path therethrough defined at one end by the air entry and at the opposing end by the aerosol port. The air path can extend through the radiation-trapping chamber. The air path can be substantially a straight line.

The aerosol delivery device can comprise one or more of an electrical power source, a pressure sensor, and a microcontroller.

One or more of the electrical power source, the pressure sensor, and the microcontroller can be positioned within a control housing that is connectable with the outer shell.

In some embodiments, an aerosol delivery device according to the present disclosure can comprise an outer shell and a heater configured for vaporizing an aerosol precursor composition, the heater comprising a laser diode. The aerosol delivery device may be defined by one or more further characteristics, the following statements being exemplary thereof and being combinable in any manner.

The aerosol delivery device can comprise one or more of an electrical power source, a pressure sensor, and a microcontroller.

One or more of the electrical power source, the pressure sensor, and the microcontroller can be positioned within a control housing that is connectable with the outer shell.

The outer shell can comprise an air entry and can comprise a mouthend with an aerosol port.

The aerosol delivery device can comprise an air path therethrough defined at one end by the air entry and at the opposing end by the aerosol port. The air path can be substantially a straight line.

The aerosol delivery device can comprise a wick configured to deliver the aerosol precursor composition from a reservoir to be in a vaporizing arrangement with the heater.

The aerosol delivery device can comprise a radiation-trapping chamber with a chamber wall, wherein the heater is positioned within the radiation-trapping chamber. The heater can be positioned on or in the chamber wall. The heater can be positioned away from the chamber wall.

The wick can pass through at least one aperture in the chamber wall of the radiation-trapping chamber such that a first section of the wick is positioned exterior to the radiation-trapping chamber and a second section of the wick is positioned interior to the radiation-trapping chamber.

The wick can be configured as a layer lining at least a portion of an interior of the chamber wall of the radiation-trapping chamber.

The radiation-trapping chamber can be substantially spherical.

The radiation-trapping chamber can be substantially elongated (e.g., substantially tubular).

An interior of the radiation-trapping chamber (e.g., an interior surface of the wall forming the chamber or a surface of a wall within the chamber) can be configured to one or more of absorb, emit, and reflect radiation from the radiation source.

The interior of the radiation-trapping chamber can be configured as a black body.

The interior of the radiation-trapping chamber can be configured as a white body.

In one or more embodiments, an aerosol delivery device can comprise: a housing; an aerosol precursor liquid; a first heater having a heating surface; a second heater having a heating surface; and a liquid transport element having at least one end in a wicking arrangement with the aerosol precursor liquid; and the first heater and the second heater can be aligned in a substantially parallel arrangement with a portion of the fluid transport element positioned therebetween. The aerosol delivery device may be defined by one or more further characteristics, the following statements being exemplary thereof and being combinable in any manner.

The aerosol precursor liquid can be physically separated from the first heater and the second heater by at least one wall. In particular, the at least one wall can at least partially define a chamber storing the aerosol precursor liquid. In some embodiments, the chamber storing the aerosol precursor liquid can be substantially annularly arranged relative to the housing.

The chamber storing the aerosol precursor liquid can be refillable.

There can be at least one wall physically separating the aerosol precursor liquid from the first heater and the second heater can include at least one aperture through which the at least one end of the liquid transport element extends. In particular, the at least one aperture can include a leak resistive gasket.

The first heater and the second heater can be arranged apart so as to define an aerosol forming space therebetween.

The can be first heater and the second heater can be arranged such that the aerosol forming space is substantially parallel to a longitudinal axis of the housing.

The device can include and airflow path through the housing, said airflow path extending through a space defined between the first heater and the second heater and to an aerosol outlet of the housing.

The device further can comprise one or more of a controller, a power source, and a flow sensor.

The aerosol delivery device further can comprise a second housing that is connectable with the housing, and wherein one or more of the controller, power source, and flow sensor is positioned in the second housing.

In some embodiments, the present disclosure can provide an atomizer for an aerosol delivery device. In particular, the atomizer can comprise a radiation-trapping chamber formed of a chamber wall, a radiation source positioned within the radiation-trapping chamber, and a wick, at least a portion of which is positioned within the radiation-trapping chamber so as to be in a vaporizing arrangement with the heater. The atomizer may be defined by one or more further characteristics, the following statements being exemplary thereof and being combinable in any manner.

The radiation-trapping chamber can be substantially spherical.

The radiation-trapping chamber can be substantially elongated (e.g., may be substantially tubular).

An interior of the radiation-trapping chamber (e.g., an interior surface of the wall forming the chamber or a surface of a wall within the chamber) can be configured to one or more of absorb, emit, and reflect radiation from the radiation source.

The interior of the radiation-trapping chamber can be configured as a black body.

The interior of the radiation-trapping chamber can be configured as a white body.

The radiation source can comprise a laser diode.

The radiation source can comprise a resistive heating wire.

In one or more embodiments, an atomizer for an aerosol forming device can comprise: a first heater having a heating surface; a second heater having a heating surface; and a liquid transport element; and the first heater and the second heater can be aligned in a substantially parallel arrangement with the fluid transport element positioned therebetween. The atomizer may be defined by one or more further characteristics, the following statements being exemplary thereof and being combinable in any manner.

The first heater and the second heater can be spaced apart with the respective heating surfaces facing each other.

The liquid transport element may expressly not be in direct contact with either of the first heater and the second heater.

The first heater and the second heater can have a substantially flattened shape.

The first heater and the second heater each can comprise a substrate with a heating trace on a surface so as to define the heating surface. If desired, the heating surface of each of the first heater and the second heater further can comprises a passivating layer over the heater trace.

The liquid transport element can comprise a ceramic material.

The liquid transport element can comprise a fibrous material.

The liquid transport element can comprise a rigid porous structure that contains an open pore network (i.e., porous glass, sintered porous glass beads, sintered porous ceramic beads, porous carbon, or graphite).

The liquid transport element can comprise opposing ends. In particular, at least one of the opposing ends of the liquid transport element can extend away from the first heater and the second heater so as to not be in a heating arrangement with the first heater and the second heater.

The atomizer can further comprise an atomizer housing formed of at least one wall enclosing the first heater element and the second heater element.

The atomizer housing can comprises at least one aperture through which the liquid transport element extends.

The atomizer housing can include a leak resistive gasket at the at least one aperture.

The atomizer housing can comprise an air inlet and an aerosol outlet.

In some embodiments, the present disclosure can relate to methods of forming an aerosol delivery device. For example, such method can comprise inserting an atomizer into an outer shell, the atomizer comprising a radiation-trapping chamber and a heater configured to provide electromagnetic radiation. The atomizer further can comprise a wick, which may pass through an aperture into the radiation-trapping chamber and/or which may substantially line an interior surface of the chamber, such as an interior surface of the wall forming the radiation-trapping chamber. The method can comprise establishing an electrical connection between the heater and one or more electrical contacts. The electrical contacts may be configured to provide electrical connection between the heater and a power source, which may be positioned within the outer shell or may be positioned within a separate control body, which may be connectable to the outer shell so as to form the electrical connection. The method may comprise inserting a reservoir within the outer shell such that the wick is in fluid communication with an aerosol precursor composition stored within the reservoir.

In one or more embodiments, the disclosure can relate to methods of forming a vapor for inhalation. For example, such method can comprise: supplying an aerosol precursor liquid along a liquid transport element, a portion of the liquid transport element being positioned between a first heater and a second heater that are aligned in a substantially parallel arrangement; and providing power to the first heating element and the second heating element sufficient to cause the first heater and the second heater to heat and vaporize at least a portion of the aerosol precursor liquid supplied along the liquid transport element. The method may be defined by one or more further characteristics, the following statements being exemplary thereof and being combinable in any manner.

The first heater and the second heater can be spaced apart so as to define an aerosolization space therebetween, the liquid transport element being positioned within the aerosolization space, and wherein the liquid transport element is not in physical contact with either of the first heater and the second heater.

The heating of the aerosol precursor liquid supplied along the liquid transport element can be substantially only by radiant heating from the first heater and the second heater.

BRIEF DESCRIPTION OF THE FIGURES

Figure 1:
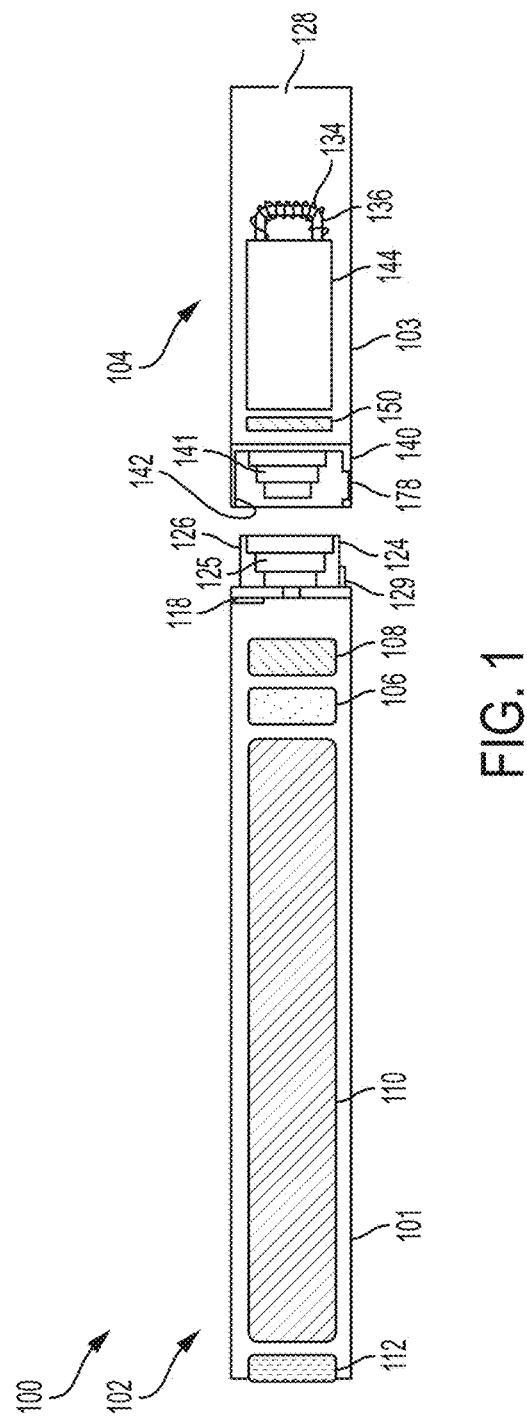
Figure 2A:
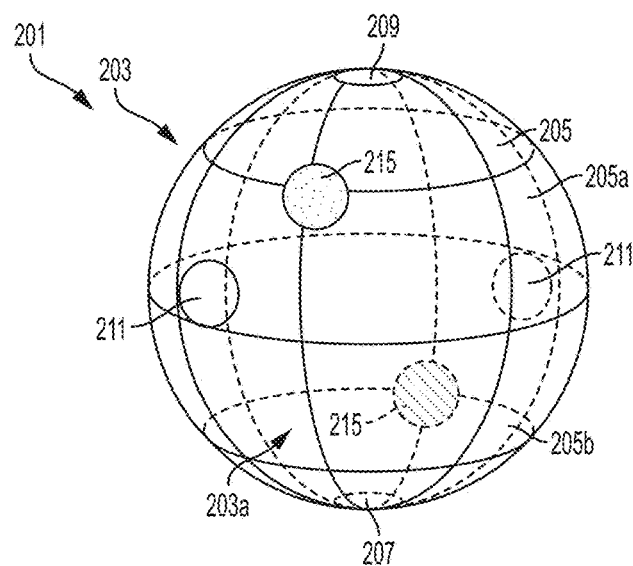
Figure 2B:
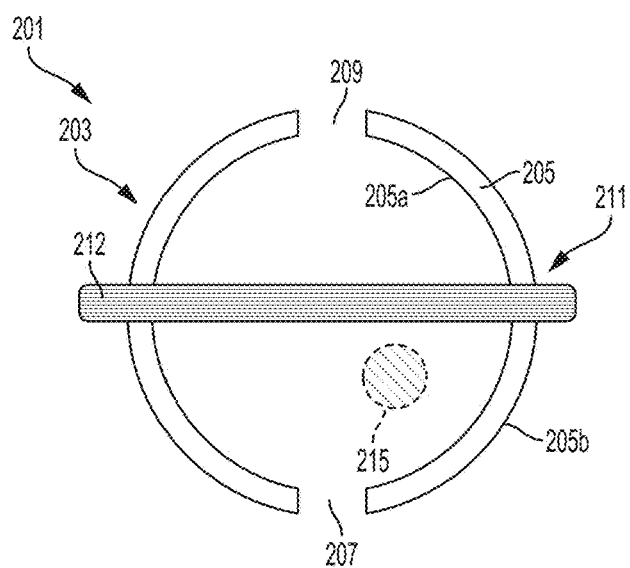
Figure 2C:
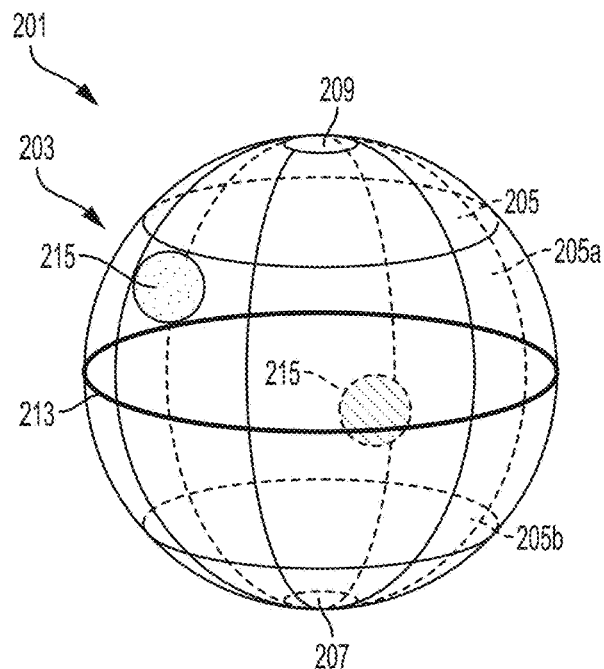
Figure 2D:
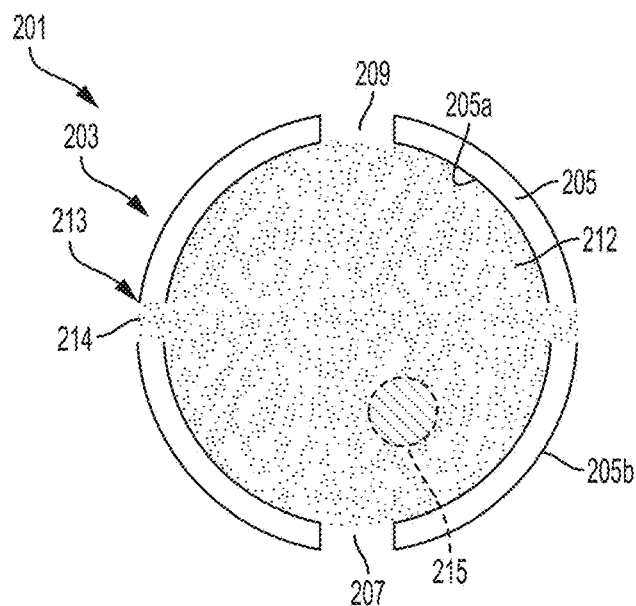
Figure 3:
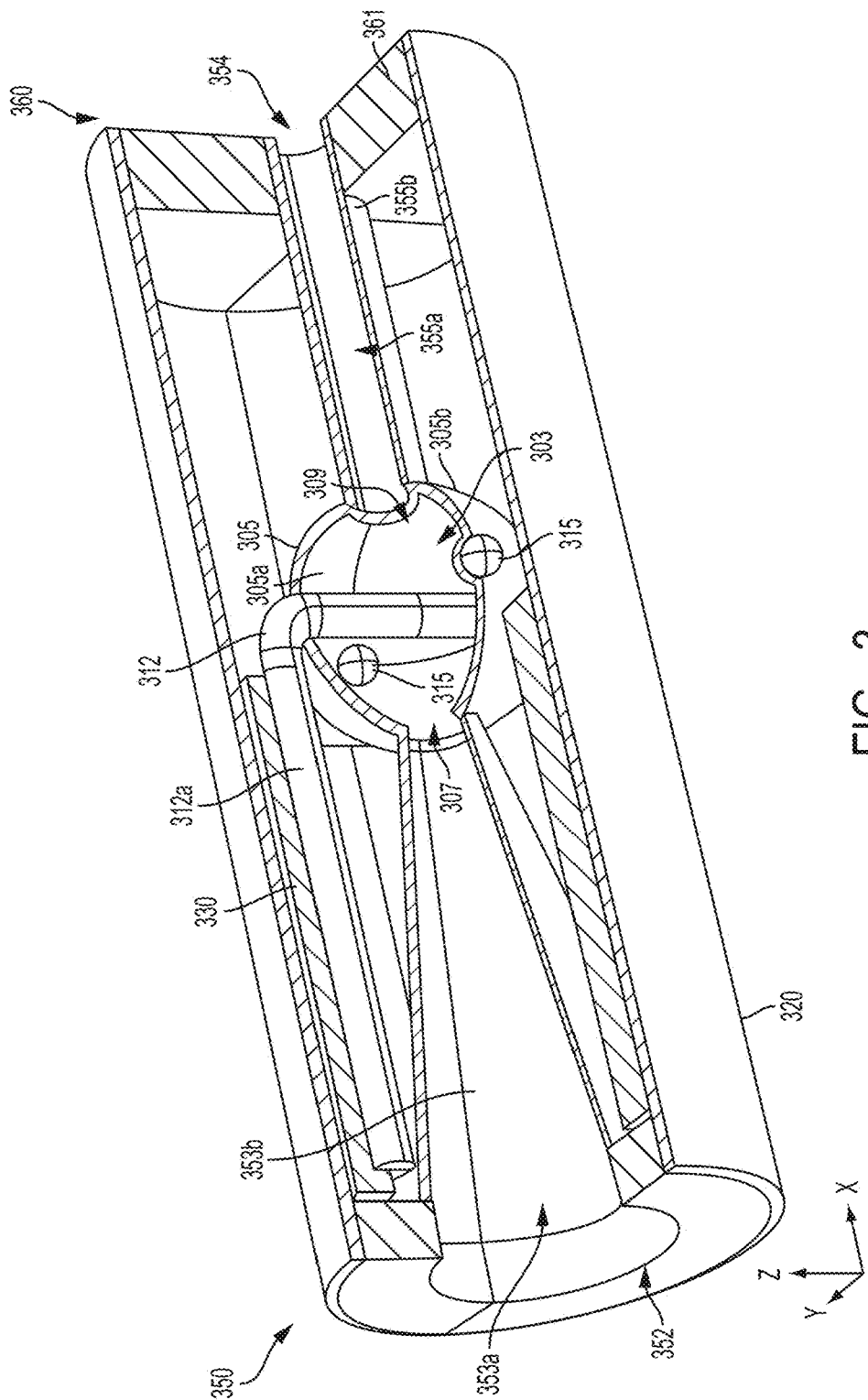
Figure 3A:
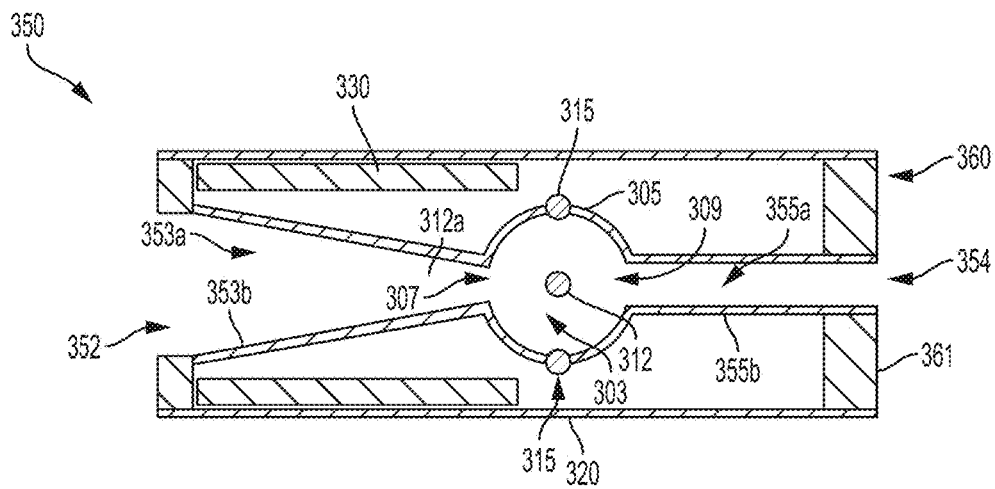
Figure 3B:
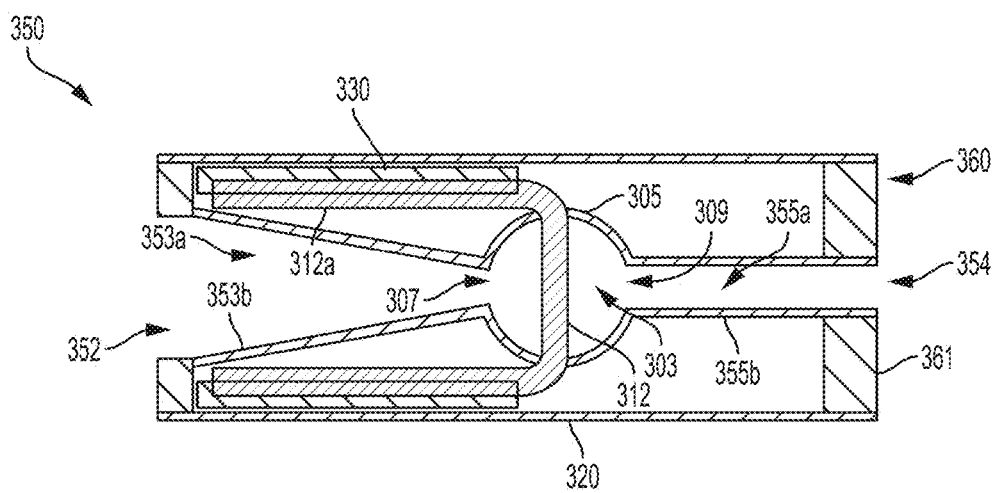
Figure 4:
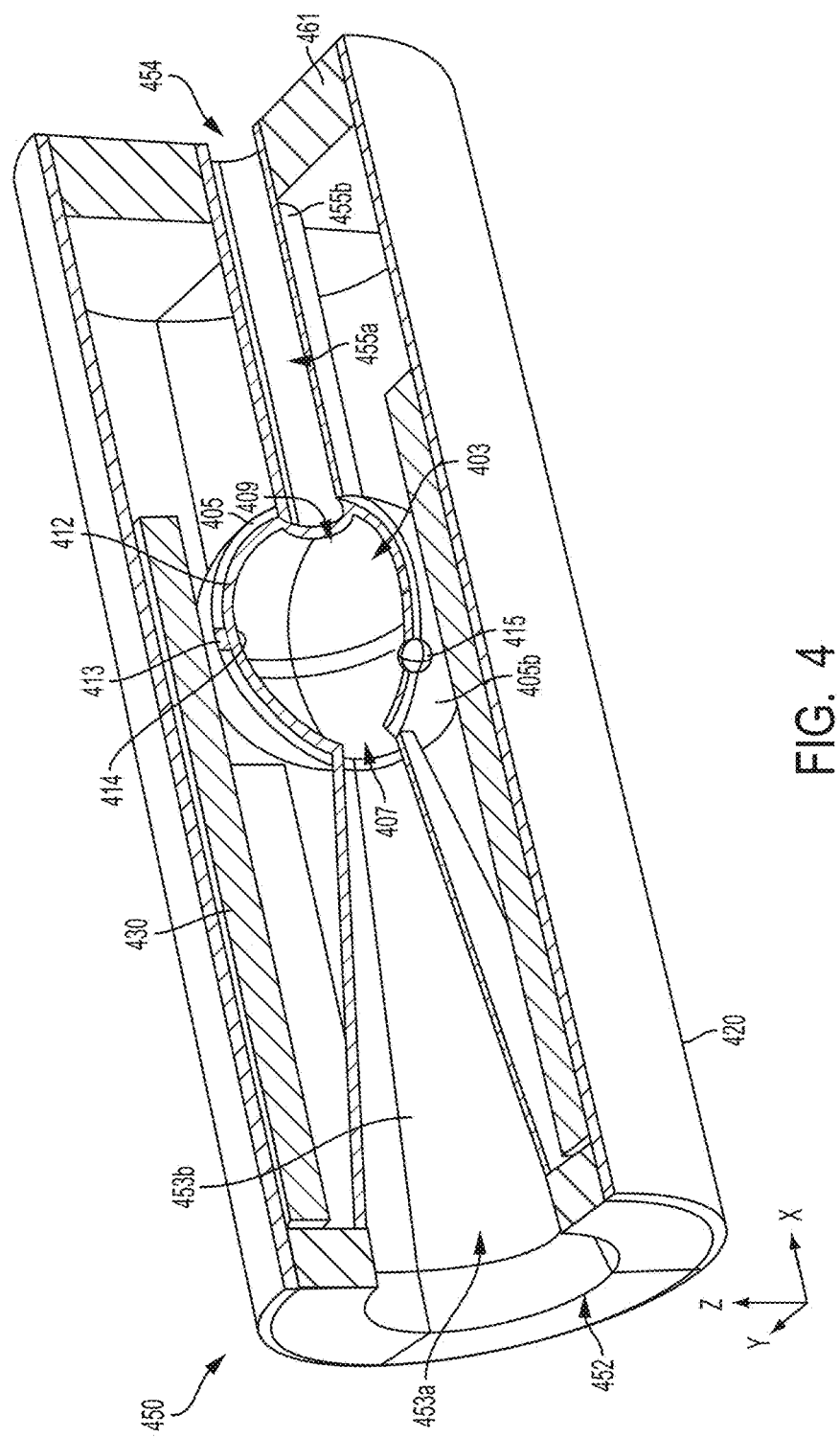
Figure 5:
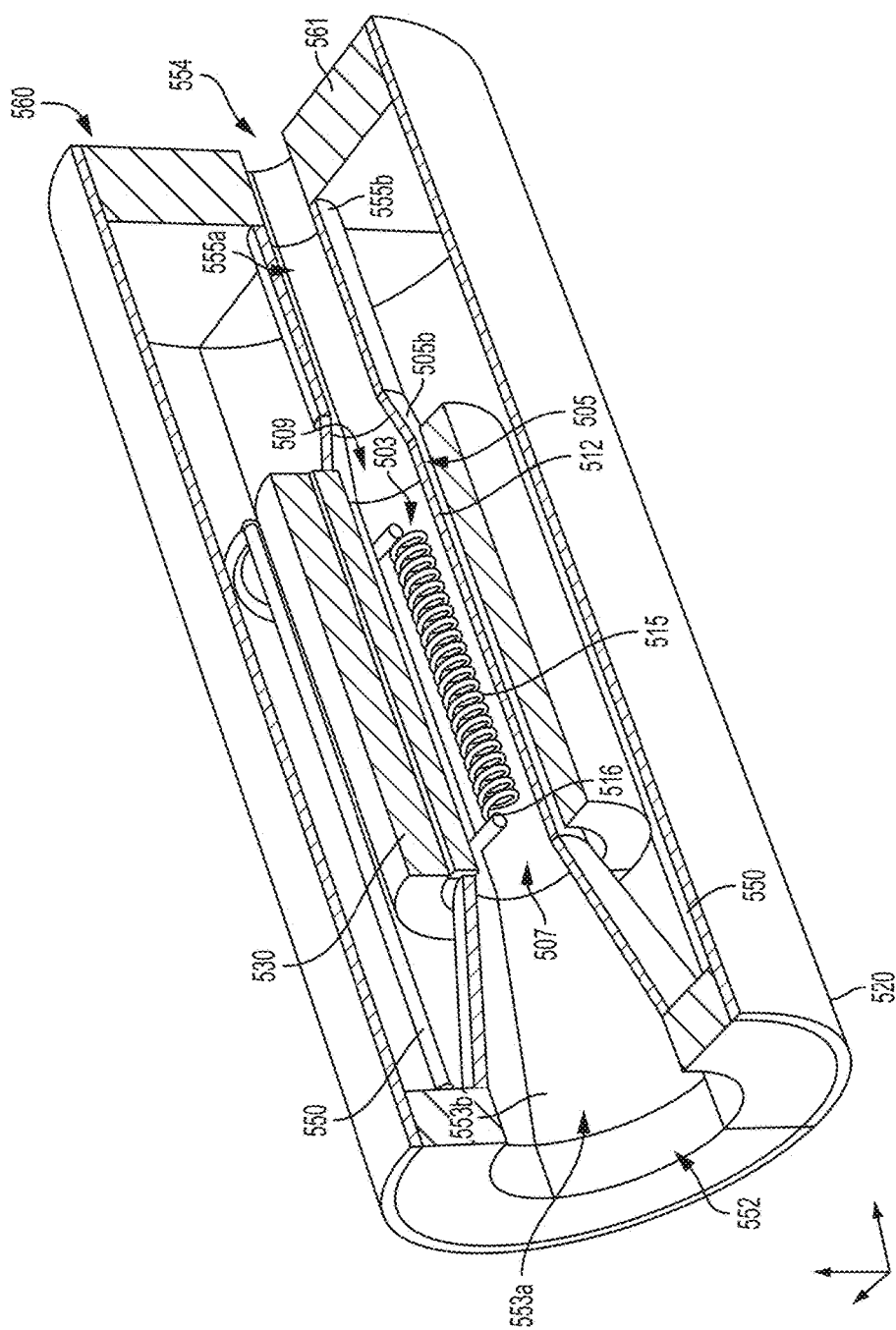
Figure 5A:
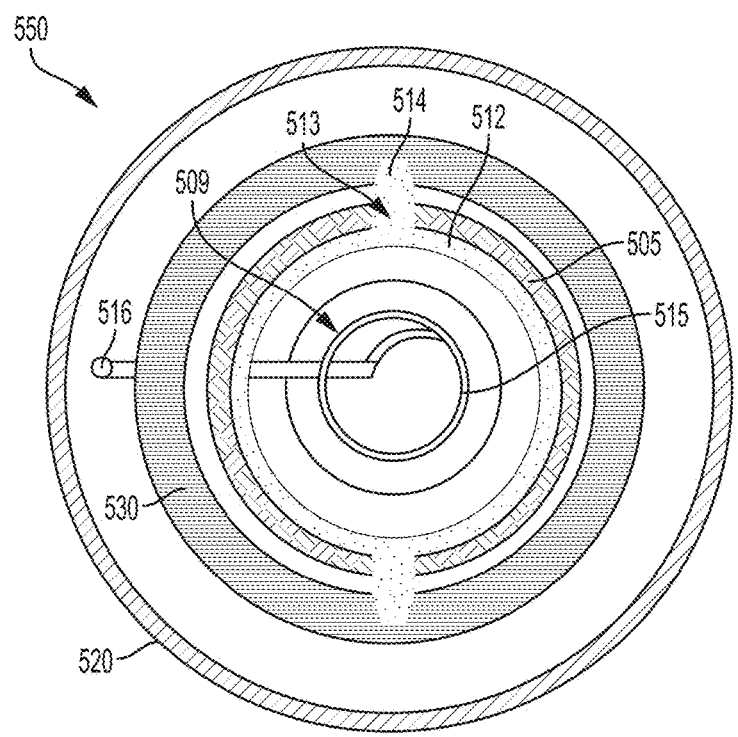
Figure 6:
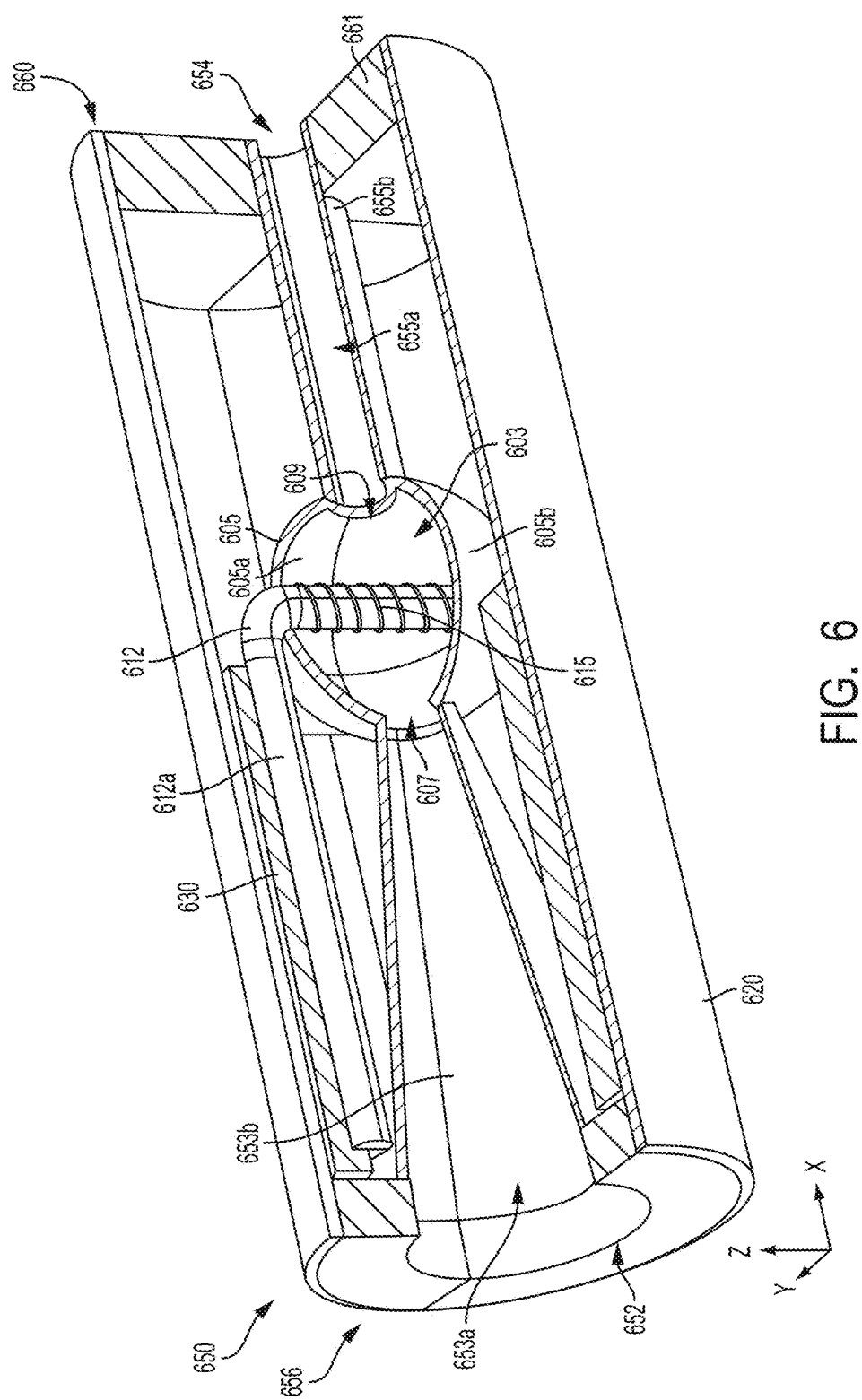
Figure 7A:
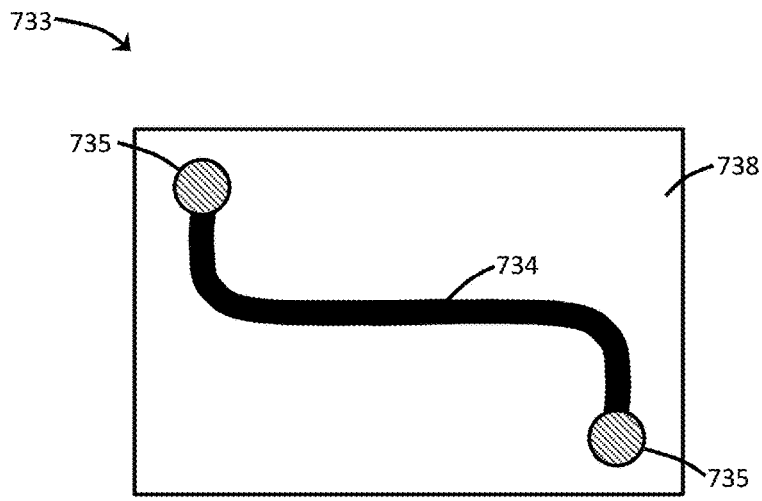
Figure 7B:
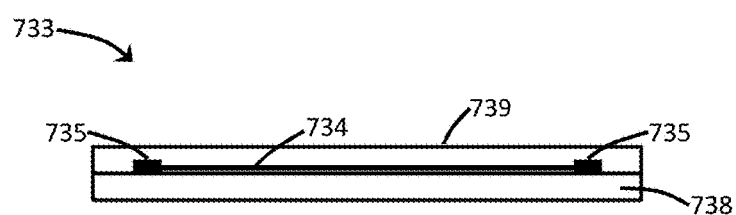
Figure 8:
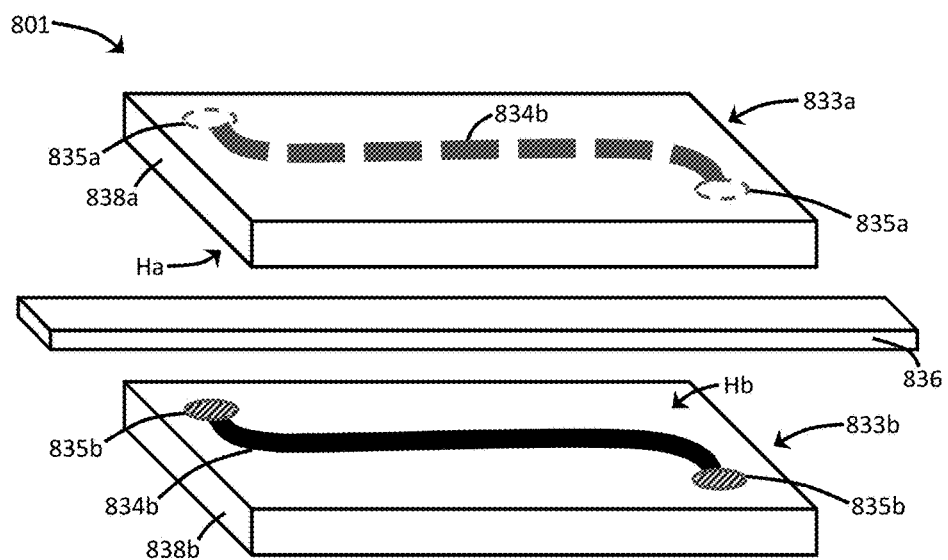
Figure 9A:
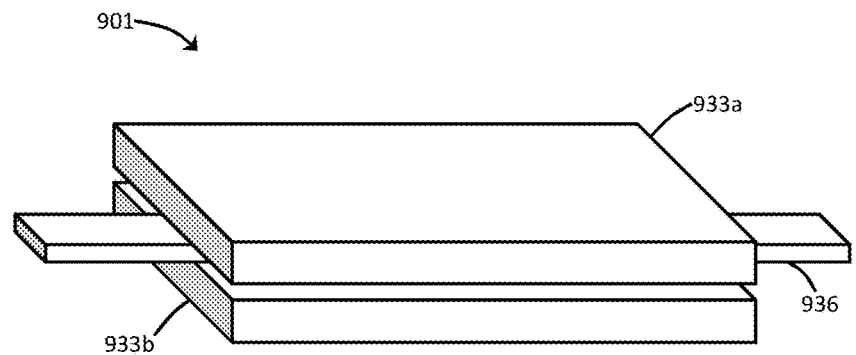
Figure 9B:
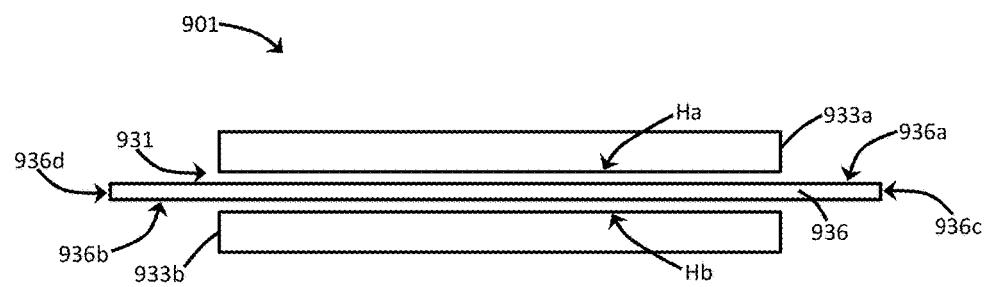
Figure 9C:
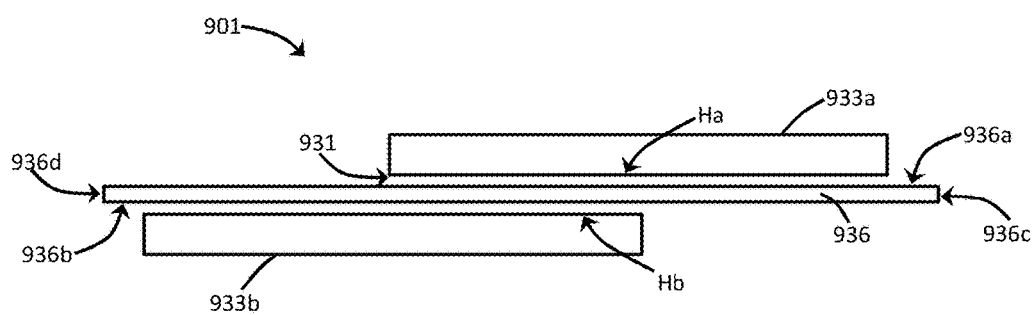
Figure 10A:
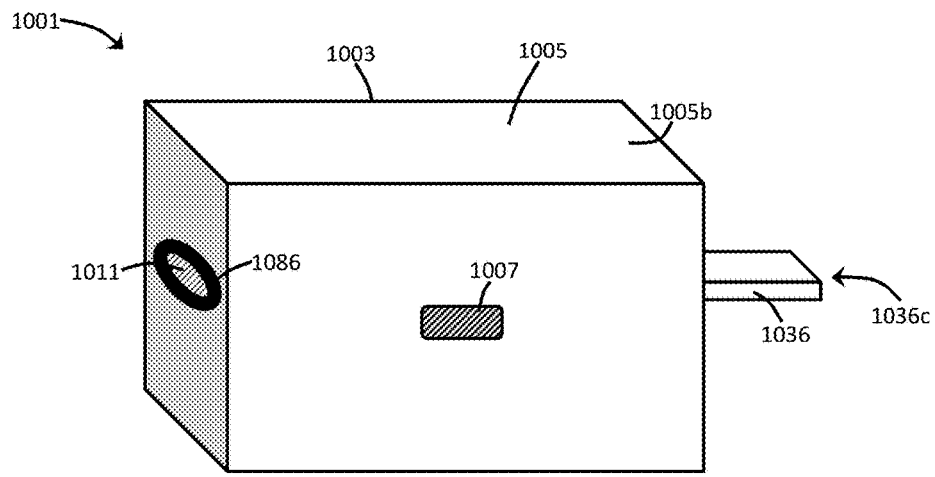
Figure 10B:
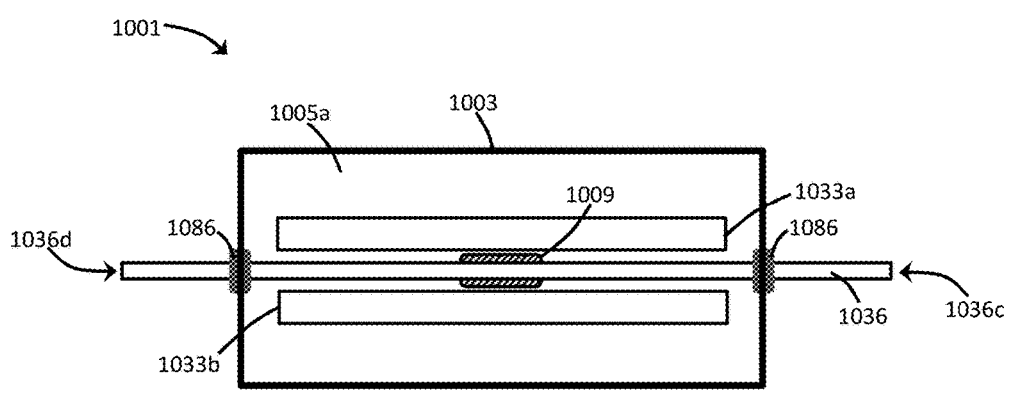
Figure 11:
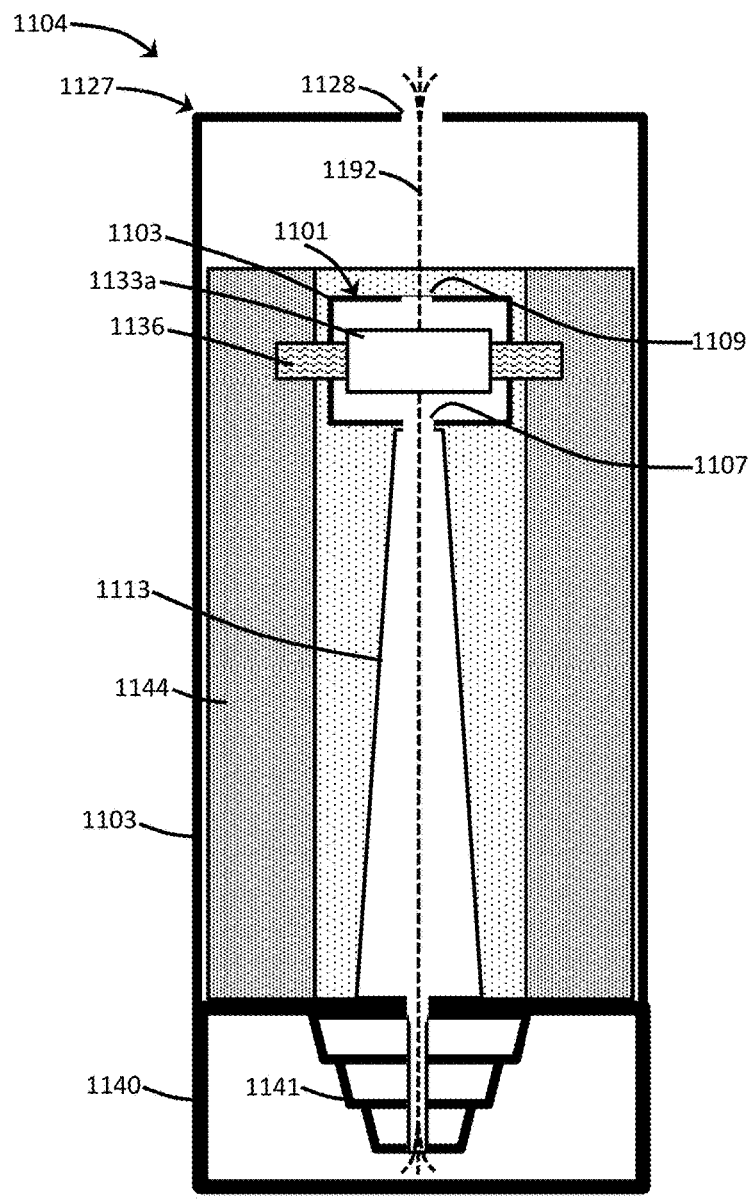
Figure 12:
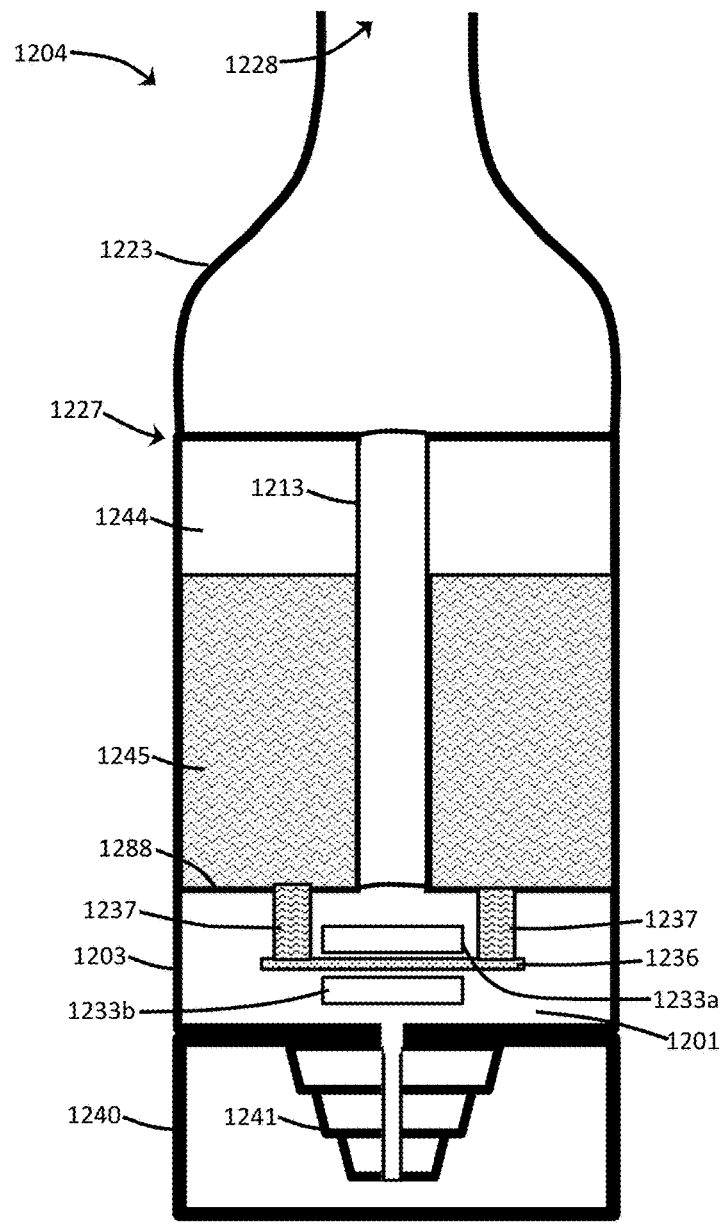

Having thus described the disclosure in the foregoing general terms, reference will now be made to the accompanying drawings, which are not necessarily drawn to scale, and wherein:

FIG. 1 is a partially cut-away view of an aerosol delivery device comprising a cartridge and a control body including a variety of elements that may be utilized in an aerosol delivery device according to various embodiments of the present disclosure;

FIG. 2a is a partially transparent view of a radiation-trapping chamber with wick apertures for use as an atomizer according to example embodiments of the present disclosure;

FIG. 2b is a cross-sectional view of an atomizer according to example embodiments of the present disclosure including a radiation-trapping chamber, a radiation source, and a wick;

FIG. 2c is a partially transparent view of a radiation-trapping chamber with a channel therein for use as an atomizer according to example embodiments of the present disclosure;

FIG. 2d is a cross-sectional view of an atomizer according to example embodiments of the present disclosure including a radiation-trapping chamber, a radiation source, and a wick;

FIG. 3 is a partially cut away, perspective view of an aerosol delivery device according to an example embodiments of the present disclosure;

FIG. 3a is a cross-sectional view through the xy plane of the aerosol delivery device illustrated in FIG. 3;

FIG. 3b is a cross-sectional view through the xz plane of the aerosol delivery device illustrated in FIG. 3;

FIG. 4 is a partially cut away, perspective view of a further aerosol delivery device according to example embodiments of the present disclosure;

FIG. 5 is a partially cut away, perspective view of yet another aerosol delivery device according to example embodiments of the present disclosure;

FIG. 5a is a cross-sectional view through the yz plane of the aerosol delivery device illustrate in FIG. 5;

FIG. 6 is a partially cut away, perspective view of still another aerosol delivery device according to example embodiments of the present disclosure;

FIG. 7a is a top view of a microheater suitable for use in a device according to example embodiments of the present disclosure;

FIG. 7b is a side view of a microheater suitable for use in a device according to example embodiments of the present disclosure;

FIG. 8 is a perspective, exploded view of an atomizer according to example embodiments of the present disclosure, the atomizer including a first heater, a second heater, and a liquid transport element therebetween;

FIG. 9a is a perspective view of an atomizer according to example embodiments of the present disclosure, the atomizer including a first heater, a second heater, and a liquid transport element therebetween;

FIG. 9b is a side view of the atomizer of FIG. 9a;

FIG. 9c is a side view of the atomizer of FIG. 9a with the heaters adjusted positionally so as to be out of direct alignment;

FIG. 10a is a perspective view of an atomizer according to example embodiments of the present disclosure, the atomizer including a chamber having two heaters therein and a liquid transport element positioned between the two heaters and extending out of the chamber;

FIG. 10b is a partial cross-section of the atomizer of FIG. 10a;

FIG. 11 is a partial cross-section of an aerosol delivery device according to example embodiments of the present disclosure, the device including a fibrous reservoir with an aerosol precursor liquid absorbed and/or adsorbed therein; and FIG. 12 is a partial cross-section of an aerosol delivery device according to example embodiments of the present disclosure, the device including a reservoir tank holding an aerosol precursor liquid.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body comprising a housing containing one or more components (e.g., a battery and various electronics for controlling the operation of that article), and at the other end and removably attached thereto an outer body or shell containing aerosol forming components (e.g., one or more aerosol precursor components, such as flavors and aerosol formers, one or more heaters, and/or one or more wicks).

Aerosol delivery devices of the present disclosure can be formed of an outer housing or shell that is not substantially tubular in shape but may be formed to substantially greater dimensions. The housing or shell can be configured to include a mouthpiece and/or may be configured to receive a separate shell (e.g., a cartridge) that can include consumable elements, such as a liquid aerosol former, and can include a vaporizer or atomizer.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller or microprocessor), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

One example embodiment of an aerosol delivery device 100 illustrating components that may be utilized in an aerosol delivery device according to the present disclosure is provided in FIG. 1. As seen in the cut-away view illustrated therein, the aerosol delivery device 100 can comprise a control body 102 and a cartridge 104 that can be permanently or detachably aligned in a functioning relationship. Engagement of the control body 102 and the cartridge 104 can be press fit (as illustrated), threaded, interference fit, magnetic, or the like. In particular, connection components, such as further described herein may be used. For example, the control body may include a coupler that is adapted to engage a connector on the cartridge.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. Pat. Pub. No. 2014/0261495 to Novak et al., which is incorporated herein by reference in its entirety. Further, in some embodiments the cartridge may comprise a single-use cartridge, as disclosed in U.S. Pat. No. 8,910,639 to Chang et al., which is incorporated herein by reference in its entirety.

As illustrated in FIG. 1, a control body 102 can be formed of a control body shell 101 that can include a control component 106 (e.g., a printed circuit board (PCB), an integrated circuit, a memory component, a microcontroller, or the like), a flow sensor 108, a battery 110, and an LED 112, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

A cartridge 104 can be formed of a cartridge shell 103 enclosing the reservoir 144 that is in fluid communication with a liquid transport element 136 adapted to wick or otherwise transport an aerosol precursor composition stored in the reservoir housing to a heater 134. A liquid transport element can be formed of one or more materials configured for transport of a liquid, such as by capillary action. A liquid transport element can be formed of, for example, fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element thus can be any material that contains an open pore network (i.e., a plurality of pores that are interconnected so that fluid may flow from one pore to another in a plurality of direction through the element). Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). As further described herein, a heater may comprise a variety of materials configured to provide electromagnetic radiation, including laser diodes.

An opening 128 may be present in the cartridge shell 103 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 150, which may include an integrated circuit, a memory component, a sensor, or the like. The electronic component 150 may be adapted to communicate with the control component 106 and/or with an external device by wired or wireless means. The electronic component 150 may be positioned anywhere within the cartridge 104 or its base 140.

Although the control component 106 and the flow sensor 108 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some embodiments, the air flow sensor may comprise its own circuit board or other base element to which it can be attached. In some embodiments, a flexible circuit board may be utilized. A flexible circuit board may be configured into a variety of shapes, include substantially tubular shapes.

The control body 102 and the cartridge 104 may include components adapted to facilitate a fluid engagement therebetween. As illustrated in FIG. 1, the control body 102 can include a coupler 124 having a cavity 125 therein. The cartridge 104 can include a base 140 adapted to engage the coupler 124 and can include a projection 141 adapted to fit within the cavity 125. Such engagement can facilitate a stable connection between the control body 102 and the cartridge 104 as well as establish an electrical connection between the battery 110 and control component 106 in the control body and the heater 134 in the cartridge. Further, the control body shell 101 can include an air intake 118, which may be a notch in the shell where it connects to the coupler 124 that allows for passage of ambient air around the coupler and into the shell where it then passes through the cavity 125 of the coupler and into the cartridge through the projection 141.

A coupler and a base useful according to the present disclosure are described in U.S. Pat. Pub. No. 2014/0261495 to Novak et al., the disclosure of which is incorporated herein by reference in its entirety. For example, a coupler as seen in FIG. 1 may define an outer periphery 126 configured to mate with an inner periphery 142 of the base 140. In one embodiment the inner periphery of the base may define a radius that is substantially equal to, or slightly greater than, a radius of the outer periphery of the coupler. Further, the coupler 124 may define one or more protrusions 129 at the outer periphery 126 configured to engage one or more recesses 178 defined at the inner periphery of the base. However, various other embodiments of structures, shapes, and components may be employed to couple the base to the coupler. In some embodiments the connection between the base 140 of the cartridge 104 and the coupler 124 of the control body 102 may be substantially permanent, whereas in other embodiments the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, multifaceted shapes, or the like.

The reservoir 144 illustrated in FIG. 1 can be a container or can be a fibrous reservoir, as presently described. For example, the reservoir 144 can comprise one or more layers of nonwoven fibers substantially formed into the shape of a tube encircling the interior of the cartridge shell 103, in this embodiment. An aerosol precursor composition can be retained in the reservoir 144. Liquid components, for example, can be sorptively retained by the reservoir 144. The reservoir 144 can be in fluid connection with a liquid transport element 136. The liquid transport element 136 can transport the aerosol precursor composition stored in the reservoir 144 via capillary action to the heating element 134 that is in the form of a metal wire coil in this embodiment. As such, the heating element 134 is in a heating arrangement with the liquid transport element 136.

In use, when a user draws on the article 100, airflow is detected by the sensor 108, the heating element 134 is activated, and the components for the aerosol precursor composition are vaporized by the heating element 134. Drawing upon the mouthend of the article 100 causes ambient air to enter the air intake 118 and pass through the cavity 125 in the coupler 124 and the central opening in the projection 141 of the base 140. In the cartridge 104, the drawn air combines with the formed vapor to form an aerosol. The aerosol is whisked, aspirated, or otherwise drawn away from the heating element 134 and out the mouth opening 128 in the mouthend of the article 100.

An input element may be included with the aerosol delivery device. The input may be included to allow a user to control functions of the device and/or for output of information to a user. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some embodiments, an input may comprise a computer or computing device, such as a smartphone or tablet. In particular, the aerosol delivery device may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device can incorporate a sensor or detector for control of supply of electric power to the heat generation element when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collet et al., and 2014/0270727 to Ampolini et al.; and U.S. patent application Ser. No. 14/209,191, filed Mar. 13, 2014, to Henry et al.; which are incorporated herein by reference.

Representative types of substrates, reservoirs or other components for supporting the aerosol precursor are described in U.S. Pat. No. 8,528,569 to Newton; U.S. Pat. Pub. Nos. 2014/0261487 to Chapman et al. and 2014/0059780 to Davis et al.; and U.S. patent application Ser. No. 14/170,838, filed Feb. 3, 2014, to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 1 or as otherwise described above may be included in an aerosol delivery device according to the present disclosure.

In some embodiments, the present disclosure particularly can relate to atomizers and elements thereof that may be utilized in an aerosol delivery device. Such atomizers and elements thereof can be particularly beneficial for improved energy efficiency in an aerosol delivery device. For example, energy drain associated with achieving the desired heating temperature between puffs on a device can be minimized. More particularly, the atomizers and associated elements can achieve the desired heating temperature more rapidly and/or reduce heat losses that may hinder vaporization.

In some embodiments, the heater used in an atomizer can be a source of electromagnetic radiation. In particular, the heater can be configured to emit electromagnetic radiation of a specific wavelength or a specific range of wavelengths (i.e., a defined band). For example, the heater can be configured to emit electromagnetic radiation having a wavelength that is within the range that encompasses violet light to far infrared light. More particularly, the wavelength can be within the range of about 390 nm to about 1 mm. As another example, the wavelength can be within the range that encompasses visible light (i.e., about 400 nm to about 700 nm).

The radiation source may be configured to emit radiation with a focused band, and such focused band may be chosen based upon the substrate to be heated so as to maximize the heating of the specific substrate(s). For example, the radiation source can be configured to emit electromagnetic radiation within a wavelength band having a bandwidth that is no greater than 100 µm, that is no greater than 10 µm, no greater than 1,000 nm, that is no greater than 500 nm, that is no greater than 250 nm, that is no greater than 100 nm, that is no greater than 50 nm, that is no greater than 10 nm, that is no greater than 5 nm, or that is no greater than 2 nm. More particularly, the radiation source can be configured to emit electromagnetic radiation within a range corresponding to a particular absorption wavelength of a wick material, of an aerosol precursor composition, and/or of one or more specific components of an aerosol precursor composition. As a non-limiting example, many polyols that may be used in an aerosol precursor composition can exhibit preferential absorption in a wavelength band of about 2 µm to about 12 µm. Thus, a heater according to the present disclosure may be configured to emit electromagnetic radiation within a wavelength band that is no greater than 10 µm (i.e., having specific wavelengths in the range of 2 µm to 12 µm). Other ranges, however, are encompassed. For example a wavelength band of about 700 nm to about 1 mm may be beneficial for specific absorbance of electromagnetic energy of visible by a material that is visibly clear but is opaque in relation to infrared light. As yet a further example, a wavelength band of about 390 nm to about 790 nm may be beneficial for specific absorbance by a substrate that is visibly black. In some embodiments, a laser diode may be used as the heater. Utilization of radiation of a specific wavelength or very narrow band (such as is common in a laser) can focus the energy spectrally so that less energy is spread out to various wavelengths. Radiation wavelength also can be more specifically tuned to a specific absorption wavelength (or band) of a substrate, such as an aerosol precursor composition or component thereof and/or a wick from which the aerosol precursor composition may be vaporized. Use of a laser-based radiation source also can be advantageous for focusing the radiation energy into a smaller space-domain to minimize radiation losses.

An atomizer according to the present disclosure can be defined in some embodiments by a chamber within which the radiation is emitted and from which vaporized aerosol precursor composition may be released. When a laser radiation source in particular is utilized, the chamber may be reduced in size because of the ability to focus the radiation energy and avoid energy losses. Thus, the desired amount of vapor may be produced from a smaller volume since less energy is wasted. In some embodiments, a laser radiation source can provide direct heating of an aerosol precursor composition. For example, a device may be configured such that aerosol precursor composition is delivered (including via wicking) to a specific location (i.e., a vaporization target) within a chamber, and one or more laser radiation sources can be focused directly at the specific location. In this manner, less radiation is available for scattering within the chamber, but a majority of the radiation directly strikes the vaporization target. In embodiments wherein the laser radiation band is focused to a preferred absorption wavelength of the target (i.e., the target substrate and/or the aerosol precursor material), such focused heating may be particularly beneficial for increasing vapor formation while reducing energy requirements.

The chamber may take on a variety of shapes. For example, the chamber may be substantially spherical. Multifaceted structures may also be utilized. In some embodiments, the chamber may be substantially elongated (e.g., tubular). Chamber shape (optionally in combination with the airflow path through and/or around the chamber) can enhance not only the energy absorption but also vapor elution.

The chamber can, in some embodiments, be a radiation-trapping chamber. The chamber preferentially is configured to maximize the capture and/or release of incident radiation on the chamber walls. As such, the interior of the wall(s) forming the chamber can be configured to one or more of absorb, emit, and reflect radiation from the radiation source. For example: the interior of the chamber wall(s) may be configured to absorb at least about 50%, at least about 60%, at least about 70%, or at least about 80% of all incident electromagnetic radiation; the interior of the chamber wall (s) may be configured to reflect at least about 50%, at least about 60%, at least about 70%, or at least about 80% of all incident electromagnetic radiation.

In some embodiments, the interior of the chamber wall can be configured as a black body. In other words, the black body construction can indicate that substantially all of the incident electromagnetic radiation is absorbed, regardless of frequency or angle of incidence. The ability of the black body construction to absorb substantially all of the incident electromagnetic radiation can mean that at least 98%, at least 99%, at least 99.5%, or at least 99.9% of all incident electromagnetic radiation is absorbed. The black body construction further can indicate that it is an ideal emitter (i.e., at every frequency, it emits as much (or more) energy as any other body at the same temperature) and/or that it is a diffuse emitter (i.e., the energy is radiated isotropically, independent of direction). A black body in thermal equilibrium can emit electromagnetic radiation—i.e., black-body radiation. Such radiation is emitted having a spectrum that is determined by temperature and not by the shape or composition of the black body structure. A radiation-trapping chamber thus may be constructed of a material having an emissivity that is close to 1. For example, emissivity of a radiation trapping chamber configured substantially as a black body can be greater than 0.5, greater than 0.6, greater than 0.7, greater than 0.8, or greater than 0.9, such as, for example, in the range of about 0.6 to about 0.99, about 0.7 to about 0.98, or about 0.75 to about 0.95.

In other embodiments, the interior of the chamber wall can be configured as a white body. In other words, the interior of the chamber wall can be configured to reflect substantially all incident electromagnetic radiation completely and uniformly in all directions. The ability to reflect substantially all incident electromagnetic radiation can mean that at least 98%, at least 99%, at least 99.5%, or at least 99.9% of all incident electromagnetic radiation is reflected. Emissivity of a radiation trapping chamber configured substantially as a white body can be less than 0.5, less than 0.4, less than 0.3, less than 0.2, or less than 0.1, such as, for example, in the range of about 0.01 to about 0.4, about 0.02 to about 0.3, or about 0.05 to about 0.25.

A radiation trapping chamber may be formed of any material that is sufficiently heat stable at the temperatures achieved within the chamber. The radiation-trapping chamber particularly may include an out, insulating layer so as to substantially prevent or reduce radiation of heat away from the chamber. As non-limiting examples, materials that may be useful in forming a radiation-trapping chamber can include ceramics and silicon-based materials. In some embodiments, a double-walled chamber may be utilized such that an insulating material (including air) may be present between the walls.

The radiation source utilized as the heater can be configured to provide radiation within the chamber, particularly a radiation-trapping chamber. In some embodiments, the radiation source may be positioned on the wall of the chamber (i.e., attached directly thereto or incorporated therein) so as to emit the radiation directly within the chamber. In other embodiments, the radiation source can be positioned within the chamber and spaced apart from the chamber wall. For example, one or more struts or supports may extend through or from the chamber wall so that the radiation source is substantially suspended within the chamber. The radiation source may be substantially centered within the chamber or may be off-set from the approximate center of the chamber. In some embodiments, the radiation source can extend substantially along a longitudinal axis through the chamber and/or through the shell of the device in which the chamber and radiation source are positioned.

The chamber can include at least one opening (or outlet) through which formed vapor may escape or be expelled. The chamber also can include an inlet into which air or another gas may pass so as to entrain or co-mingle with formed vapor and exit through the outlet. In particular, the inlet and the outlet can be in fluid communication. The chamber may include one or more further openings, apertures, or the like through which additional elements of an atomizer and/or aerosol delivery device may pass. The further openings may also allow for influx of air. Alternatively, the further openings may be substantially sealed. In some embodiments, for example, a wick or like liquid transport element may pass through one or more openings into and/or out of the chamber. Electrical contact further may pass through the chamber wall into the chamber for providing power to a heater that may be positioned therein.

Exemplary chamber configurations are illustrated in FIG. 2a through FIG. 2d. In the exemplary embodiment of FIG. 2a, an atomizer 201 comprises a chamber 203 (preferably a radiation-trapping chamber) that is substantially spherical (although other shapes are also encompassed). The chamber 203 is illustrated partially transparent for ease of description thereof. The chamber 203 is formed of a chamber wall 205 with an interior surface 205a and an exterior surface 205b. The interior surface 205a, for example, may be configured as a black body or a white body as otherwise described herein so as to enable configuration as a radiation-trapping chamber. An inlet 207 and an outlet 209 are spaced apart so as to be substantially opposing; however, other configurations may be utilized to optimize movement of formed vapor out of the chamber 203. The positions of the inlet 207 and outlet 209 may be reversed. The chamber 203 also includes apertures 211 through which a wick (not illustrated) may be inserted. Although two apertures 211 are illustrated, only a single aperture may be used, or more than two apertures may be used (i.e., for insertion of multiple wicks). Laser diodes 215 are also present and are positioned in the wall 205 of the chamber 203 so as to emit electromagnetic radiation into the interior 203a of the chamber 203.

A cross-section of the atomizer 201 from FIG. 2a is shown in FIG. 2b. In FIG. 2b, a wick 212 is shown passing through the apertures 211 so that a portion of the wick is interior to the chamber 203 and a portion of the wick is exterior to the chamber. In use, the wick 212 can transport an aerosol precursor composition to the interior 203a of the chamber 203 so that electromagnetic radiation from the laser diode 215 can be utilized to vaporize the aerosol precursor composition to pass out of the chamber, particularly combined with air entering the chamber through the inlet 207, through the outlet 209 (e.g., as an aerosol).

A further exemplary embodiment of an atomizer 201 is shown in FIG. 2c and FIG. 2d. Again, a substantially spherical chamber 203 is formed of a chamber wall 205 having an interior surface 205a and an exterior surface 205b, and laser diodes 215 are positioned in the chamber wall along with an inlet 207 and an outlet 209. In this embodiment, the wick 212 is present substantially in the form of a sheet that is lining the interior surface 205a of the chamber wall 205. The wick 212, in particular, is in a curved, planar form. The chamber 203 also includes a channel 213 passing therethrough from the interior of the chamber to the exterior of the chamber. In the illustrated embodiment, the channel 213 is substantially at the "equator" of the sphere and extends around the entire circumference thereof so as to essentially divide the chamber 203 into two hemispheres. A wick extension 214 protrudes through the channel 213 so as to be in fluid communication with the exterior environment surrounding the chamber 203. As further illustrated herein, the wick extension 214 may contact a reservoir to cause transport of the aerosol precursor composition therefrom into the interior of the chamber 203 to "wet" the wick lining. Electromagnetic radiation from the laser diodes 215 may penetrate the wick lining 212 to facilitate the radiation-trapping effect described herein and vaporize the aerosol precursor composition in the wick.

As further described below, the chamber can take on other configurations. For example, the chamber may be substantially elongated. Likewise, the electromagnetic radiation source can take on further configurations. For example, a heating wire may be used.

An aerosol delivery device 350 including a chamber 303 and an electromagnetic radiation source 315 is shown in FIG. 3. In the illustrated embodiment, the chamber 303 is again substantially spherical; however, other chamber configurations are also encompassed, as described in greater detail below. The aerosol delivery device 350 comprises an outer shell 320 in which further portions of the device are positioned. The chamber 303 comprises a chamber wall 305 with an interior surface 305a and an exterior surface 305b.

Laser diodes 315 are positioned in the chamber wall 305 and configured to emit radiation within the chamber 303. The interior surface 305a of the chamber wall 305 is configured to trap emitted radiation as otherwise described herein. A wick 312 is positioned such that a portion of the wick is interior to the chamber 303 and a portion of the wick is exterior to the chamber. In particular one or more wick arm(s) 312a are exterior to the chamber 303 and are in contact with a reservoir 330 which, as illustrated, is a porous substrate, such as a fibrous mat (although other reservoir configurations and materials are also encompassed). The reservoir 330, as illustrated, wraps around the interior of the outer shell 320. Contact between the wick 312 and the reservoir 330 is sufficient such that an aerosol precursor composition held by the reservoir may pass to the wick for transport to the chamber 303.

The chamber 303 includes an inlet 307 through which air may enter and an outlet 309 through which formed aerosol may exit. The aerosol delivery device 350 comprises an air entry 352 and an aerosol port 354 at opposing ends thereof. Air passing into the aerosol delivery device 350 through the air entry 352 is directed to the inlet 307 of the chamber by an air passage 353a defined by an air passage wall 353b that extends between the air entry and the inlet 307. In the illustrated embodiment, the air passage wall 353b is configured such that the air passage 353a is substantially conical so as taper toward the inlet 307 of the chamber 303 and improve focusing of the incoming air into the chamber. While such configuration may be preferred, it is not required, and other configurations (including absence of the air passage wall 353b) are included. Similarly, aerosol formed in the chamber 303 through mixing of the air and vaporized aerosol precursor composition passes through the outlet 309 to the aerosol port 354. An aerosol passage 355a is defined by an aerosol passage wall 355b that extends between the outlet 309 and the aerosol port 354. As illustrated, the aerosol passage is substantially linear; however, other embodiments are also encompassed. The aerosol port 354 is positioned at a mouth end 360 of the aerosol delivery device 350, and the aerosol port 354 may particularly be defined in a mouth end cap 361.

The aerosol delivery device 350 is shown in FIG. 3 relative to its x axis, y axis, and z axis. To further illustrate the device 350, FIG. 3a shows a cross-section thereof through the xy plane, and FIG. 3b shows a cross-section thereof through the xz plane.

A further example embodiment of an aerosol delivery device 450 is shown in FIG. 4. The aerosol delivery device 450 again includes a chamber 403 and an electromagnetic radiation source 415. In the illustrated embodiment, the chamber 403 is again substantially spherical; however, other chamber configurations are also encompassed. The aerosol delivery device 450 comprises an outer shell 420 in which further portions of the device are positioned. The chamber 403 comprises a chamber wall 405 with an interior surface (which is obscured in the illustration by the wick 412 that substantially lines the interior of the chamber wall) and an exterior surface 405b. Laser diodes 415 are positioned in the chamber wall 405 and configured to emit radiation within the chamber 403. A wick 412 is present in substantially the form of a sheet lining the interior surface of the chamber wall 405. The chamber 403 is formed so as to include a channel 413 passing through the wall 405 thereof from the interior of the chamber to the exterior of the chamber. In the illustrated embodiment, the channel 413 is substantially at the "equator" of the sphere and extends around the entire circumference thereof so as to essentially divide the chamber 403 into two hemispheres. A wick extension 414 protrudes through the channel 413 so as to be in fluid communication with the exterior environment surrounding the chamber 403. In particular, the wick extension 414 is in fluid connection with the reservoir 430 in which the aerosol precursor composition is stored. Contact between the wick 414 and the reservoir 430 is sufficient such that the aerosol precursor composition held by the reservoir may pass via the wick extension 414 to the wick 412 for distribution around the interior of the chamber 403. The interior surface of the chamber wall 405 is configured to trap emitted radiation as otherwise described herein. Preferably, the structure of the wick 412 is configured so that radiation may pass therethrough for interaction with the interior surface of the chamber wall 405.

In FIG. 4, the chamber 403 includes an inlet 407 through which air may enter and an outlet 409 through which formed aerosol may exit. The aerosol delivery device 450 comprises an air entry 452 and an aerosol port 454 at opposing ends thereof. Air passing into the aerosol delivery device 450 through the air entry 452 is directed to the inlet 407 of the chamber 403 by an air passage 453a defined by an air passage wall 453b that extends between the air entry and the inlet 307. Aerosol formed in the chamber 403 passes through the outlet 409 to the aerosol port 454. An aerosol passage 455a is defined by an aerosol passage wall 455b that extends between the outlet 409 and the aerosol port 454. The aerosol port 454 is positioned at a mouth end 460 of the aerosol delivery device 450, and the aerosol port may particularly be defined in a mouth end cap 461.

Another example embodiment of an aerosol delivery device 550 is shown in FIG. 5. The aerosol delivery device 550 includes a chamber 503 that is elongated (i.e., substantially tubular) and includes an electromagnetic radiation source 515 positioned within the chamber. In the illustrated embodiment, the electromagnetic radiation source 515 is a coiled wire that can provide resistive heating; however, the wire may be provided in different configurations, and other types of electromagnetic radiation sources may be used. The electromagnetic radiation source 515 has respective ends that are connected to electrical connectors 516 that provide electrical connection to a power source.

The aerosol delivery device 550 comprises an outer shell 520 in which further portions of the device are positioned. The chamber 503 comprises a chamber wall 505 with an interior surface (which is obscured in the illustration by the wick 512 that substantially lines the interior of the chamber wall) and an exterior surface 505b. A wick 512 is present in substantially the form of a sheet lining the interior surface of the chamber wall 505. The chamber 503 is formed so as to include a channel 513 passing through the wall 505 thereof from the interior of the chamber to the exterior of the chamber. See particularly the cross-section in FIG. 5a through the yz plane at approximately a longitudinal midpoint of the chamber 503. The channel 513 may pass through the chamber wall 505 at any location and is not limited to the two locations illustrated in FIG. 5a. A wick extension 514 protrudes through the channel 513 so as to be in fluid communication with the exterior environment surrounding the chamber 503. In particular, the wick extension 514 is in fluid connection with the reservoir 530 in which the aerosol precursor composition is stored. Contact between the wick 514 and the reservoir 530 is sufficient such that the aerosol precursor composition held by the reservoir may pass via the wick extension 514 to the wick 512 for distribution around the interior of the chamber 503. The interior surface of the chamber wall 505 is configured to trap emitted radiation as otherwise described herein. Preferably, the structure of the wick 512 is configured so that radiation may pass therethrough for interaction with the interior surface of the chamber wall 505.

In FIG. 5, the elongated chamber 503 includes an inlet 507 through which air may enter and an outlet 509 through which formed aerosol may exit. The aerosol delivery device 550 comprises an air entry 552 and an aerosol port 554 at opposing ends thereof. Air passing into the aerosol delivery device 550 through the air entry 552 is directed to the inlet 507 of the chamber 503 by an air passage 553a defined by an air passage wall 553b that extends between the air entry and the inlet 507. Aerosol formed in the chamber 503 passes through the outlet 509 to the aerosol port 554. An aerosol passage 555a is defined by an aerosol passage wall 555b that extends between the outlet 509 and the aerosol port 554. The aerosol port 554 is positioned at a mouth end 560 of the aerosol delivery device 550, and the aerosol port may particularly be defined in a mouth end cap 561. In this embodiment, the heater is aligned substantially parallel to the longitudinal axis of the aerosol delivery device.

In some embodiments, heating of the wick in the chamber is carried out in the absence of any direct physical contact between the wick and a heater. As such, heating may be substantially or completely radiative.

The ability to achieve sufficient heating levels through radiative heating alone has been verified with computer models of heat flow within a substantially tube-shaped chamber (see, for example, FIG. 5) and a heating rod substantially centrally located within the tube. The heating rod reaching temperatures up to 1,200° C. resulted in radiative heating of the chamber walls within the range of 125° C. to 350° C. Such model indicated that radiative heating alone can achieve suitable temperatures for vaporization of typical aerosol precursor materials as discussed herein. More particularly, in some embodiments, radiative heating can be sufficient to heat a substrate (e.g., a wick) and/or an aerosol precursor material to a temperature of about 100° C. to about 400° C., about 125° C. to about 350° C., or about 150° C. to about 300° C. In some embodiments, radiative heating can be in a range that is above the vaporization temperature of a liquid aerosol precursor material but less than 300° C., less than 250° C., or less than 200° C.

In particular embodiments, heating may be carried out using a combination of thermal conduction (i.e., direct contact of a heating source and a wick) as well as radiative heating. Utilizing combination heating can particularly be useful for improving efficiency. When utilizing thermal conduction alone, while a portion of the heat from the heat source is conducted to the wick, a significant portion of the heat radiates away from the heat source. As such, the heat source may need to be heated to a greater temperature to sufficiently overcome the radiative heat losses and still heat the wick to the required vapor forming temperature. By enclosing a conductive heating construct in a radiation trapping chamber, however, the heat that radiates away from the heat source may be directed back to the wick. As such, less power may be required to achieve the required vapor forming temperature.

For example, as illustrated in FIG. 6, an aerosol delivery device 650 can be configured such that a heater 615 in the form of a heating wire is positioned within a chamber 603 and is wrapped around a wick 612 having a portion within the chamber and having wick arms 612*a* that are exterior to the chamber. The wick arms 612*a* are in fluid connection with the reservoir 630 so that aerosol precursor composition stored in the reservoir may pass through the wick into the chamber 603 where the aerosol precursor composition is heated and vaporized through conductive heating by being in direct contact with the heater 615 and through radiative heating by receiving the additional heat that radiates away from the heater but is returned to the wick because of the nature of the interior surface 605*a* of the wall 605 of the chamber 603.

In the embodiment illustrated in FIG. 6, the aerosol delivery device 650 includes an outer shell 620, an air entry 652 and an aerosol port 654. The air entry 652 is positioned at a connecting end 656 of the aerosol delivery device 650, which may be configured for connection to a control body (see FIG. 1). The aerosol port 654 is positioned at a mouth end 660 of the aerosol delivery device 650 and is particularly formed in a mouth end cap 661. Air passing into the aerosol delivery device 650 through the air entry 652 is directed to the inlet 607 of the chamber 603 by an air passage 653*a* defined by an air passage wall 653*b* that extends between the air entry and the inlet. Aerosol formed in the chamber 603 passes through the outlet 609 to the aerosol port 654. An aerosol passage 655*a* is defined by an aerosol passage wall 655*b* that extends between the outlet 609 and the aerosol port 654. In this embodiment, the wick portion within the chamber and the heater are aligned substantially perpendicular to the longitudinal axis of the aerosol delivery device.

In some embodiments, the present disclosure further can provide for methods of preparing an aerosol delivery device. Such methods can include combining an outer shell with a radiation-trapping chamber and/or combining an outer shell with a laser diode.

In certain embodiments, a method of assembling an aerosol delivery device can comprise at least the step of inserting a radiation-trapping chamber into an outer shell. The assembly method further can comprise one or more of the following steps:

combining a heater with the radiation-trapping chamber so that the heater is configured for providing electromagnetic radiation within the chamber;

establishing an electrical connection between the heater and one or more electrical connectors in step such that the power may be delivered from a power source to the heater;

inserting a wick into the chamber;

placing a reservoir into the outer shell such that the wick is in fluid connection with the reservoir; and adding an end cap to a mouth end of the outer shell such that the mouth end is configured for exit of aerosol from the aerosol delivery device.

In such methods, the wick may be inserted into the chamber before or after the chamber is combined with the heater and/or before or after the chamber is inserted into the outer shell. Moreover, the reservoir may be placed into the outer shell before or after inserting the chamber into the outer shell.

In one or more embodiments, a heater used according to the present disclosure can be a microheater. As a non-limiting example, a microheater 733 as shown in FIG. 7 can comprise a substrate 738, a heater trace 734 on the substrate, and electrical terminals 735 to which the heater trace connects for making an electrical connection with a power source. As seen in the side view of the microheater 733 in FIG. 7*b*, the microheater further can comprise a passivating layer 739 atop the substrate 738 and substantially or completely covering the heater trace 734 and the electrical connectors 735. As illustrated, the passivating layer 739 is substantially transparent; however, the passivating layer may otherwise be translucent or opaque. The passivating layer 739 preferably is chemically and thermally stable and will not significantly reduce heat transfer from the heater trace 734 away from the microheater 733.

As can be seen in FIG. 7b, the microheater 733 can be substantially flattened in shape. As will be understood, a substantially flattened element will have a thickness that is less than the length and less than the width of the element. A substantially flattened element also can have a thickness that is about 70% or less, about 60% or less, about 50% or less, about 40% or less, about 30% or less, or about 20% or less of one or both of the length and width of the element. For example, the length and width of the microheater can each independently be about 1.5 mm to about 20 mm, about 2 mm to about 15 mm, about 2.5 mm to about 10 mm, or about 3 mm to about 8 mm. In some embodiments, the length of the microheater can be greater than the width, and a lengthwise axis of the microheater can be substantially parallel to the lengthwise axis of an aerosol forming device in which the microheater is used. Alternatively, a lengthwise axis of the microheater can be substantially perpendicular to the lengthwise axis of an aerosol forming device in which the microheater is used. The substantially flattened nature of the microheater is further evident in relation to FIG. 8, FIG. 9a, and FIG. 9b.

In one or more embodiments, a pair of heaters can be utilized for heating an aerosol precursor liquid. Each of the heaters in the pair can include a heating surface, and such heating surface particularly can be a substantially flattened surface. As such, the heating surface may be referred to as a heating face, and the heating surface or face can have a defined area such as, for example, an area of about 3 $mm^2$ to about 400 $mm^2$, about 4 $mm^2$ to about 200 $mm^2$, about 5 $mm^2$ to about 100 $mm^2$, about 6 $mm^2$ to about 50 $mm^2$, about 7 $mm^2$ to about 30 $mm^2$, or about 8 $mm^2$ to about 20 $mm^2$. The heaters having a heating surface can particularly be microheaters; however, the present disclosure is not limited to such embodiments, and the heaters can take on any structure or nature configured for providing heating to a liquid transport element as otherwise disclosed herein.

When a pair of heaters is utilized, the respective heaters preferably can be aligned in a substantially parallel arrangement. In such parallel arrangement, it can be preferable for the heating surfaces of the respective heaters to overlap such that about 25% or greater, about 50% or greater, about 60% or greater, about 70% or greater, about 80% or greater, about 90% or greater, or about 95% or greater of the heating surface of each heater overlaps. In the substantially parallel arrangement, the heating surfaces of the respective heaters are facing one another. A liquid transport element can be positioned between the heaters in such arrangement. As such, heat can be applied to the liquid transport element from two directions. The two heaters combined with a liquid transport element can be characterized as an atomizer.

One embodiment of an atomizer 801 is shown in FIG. 8. The atomizer 801 comprises a first microheater 833a and a second microheater 833b. Although the heaters in the illustrated embodiment are microheaters, such configuration is for illustration purposes only, and it is understood that the heaters can take on other forms that are in conformity with the remaining disclosure provided herein in any number of combinations. The first microheater 833a comprises a substrate 838a with a heater trace 834b and electrical contacts 835a (the heater trace and electrical contacts being illustrated in dashed lines indicating that they are located on the underside of the substrate). The downward facing surface of the first microheater 833a functions as the heating surface "Ha" having the heater trace 834a thereon. For ease of illustration, no passivating layer is provided, and it is understood that a passivating layer may be present on one or both of the microheaters 833a and 833b. The second microheater 833b likewise comprises a substrate 838b with a heater trace 834b and electrical contacts 835b, and the upward facing surface with the heater trace 834b thereon functions as the heating surface "Hb". A liquid transport element 836 is positioned between the first microheater 833a and the second microheater 833b. As illustrated, the liquid transport element 836 is substantially flattened. Such configuration can be particularly beneficial to maximize surface area for vaporization of the aerosol precursor liquid transported therein. A substantially flattened construction can also minimize the spacing between the first microheater 833a and the second microheater 833b. As illustrated in FIG. 8, the respective microheaters are not in a final placement, and the elements are separated for ease of viewing. Once assembled, one or both of the first microheater 833a and the second microheater 833b may be in physical contact with the liquid transport element 836. In one or more embodiments, however, the first microheater 833a and the second microheater 833b can be separated so as to form a heating space therebetween, and the liquid transport element can be positioned within the heating space. As such, the atomizer 801 can be characterized in that the liquid transport element 836 may specifically not be in direct contact with either of the first microheater 833a and the second microheater 833b (or other heaters that may be used in further embodiments).

An atomizer in an assembled configuration is illustrated in FIG. 9a and FIG. 9b. In particular, the atomizer 901 comprises a first heater 933a and a second heater 933b in a substantially parallel arrangement with the heating surface Ha of the first heater and the heating surface Hb of the second heater being in a facing arrangement. The first heater 933a and the second heater 933b are aligned so that substantially 100% of the heating surface Ha of the first heater is overlapping with substantially 100% of the heating surface Hb of the second heater. As can be seen particularly in FIG. 9b, the first heater 933a and the second heater 933b are spaced apart so that a heating space 931 is present therebetween. The liquid transport element 936 is positioned within this heating space 931 and is substantially centrally located therein. In this configuration, the liquid transport element 936 does not make physical contact with either of the respective heaters. Rather, heating occurs substantially or completely via radiant heating. The heating space 931 allows for vapor formation at a top surface 936a and a bottom surface 936b of the liquid transport element 936, which is substantially flattened. The liquid transport element 936 has opposing ends 936c and 936d that extend beyond the dimensions of the heaters 933a and 933b. The opposing ends 936c and 936d of the liquid transport element 936 can be configured for contact with a reservoir wherein an aerosol precursor liquid is stored to effect wicking of the liquid to the heaters 933a and 933b.

An exemplary, alternative arrangement of an atomizer is illustrated in FIG. 9c. In the illustrated embodiment, the first heater 933a and the second heater 933b remain in a substantially parallel arrangement; however, the overlap of the respective heaters is less than 100% of the respective heating surfaces. More particularly, approximately 50% of the heating surface Ha of the first heater 933a is in an overlapping arrangement with approximately 50% of the heating surface Hb of the second heater 933b.

Heaters configured for radiant heating of a substrate, such as a liquid transport element with an aerosol precursor liquid transported thereby, can be included in an aerosol forming device in a variety of configurations. For example, a combination of two heaters with a liquid transport element therebetween, as otherwise described above, can be utilized in known aerosol forming devices in combination with, or as a replacement for, a heater and a liquid transport element used therein. In one or more embodiments, a combination of a pair of heaters and a liquid transport element can be configured so that one or both ends of the liquid transport element are in a fluid transport arrangement with a reservoir or other storage element including an aerosol precursor liquid for transport to the heaters. Accordingly, the heaters can be separated from the aerosol precursor liquid in the reservoir by one or more walls. The one or more walls can comprise part of an atomizer that includes the heaters and/or the one or more walls can comprise part of the reservoir or other liquid storage chamber/element and/or the one or more walls can be a partition that is provided between the heaters and a separate liquid storage chamber/element.

Exemplary embodiments of an atomizer are illustrated in relation to FIG. 10*a*, which shows an exterior view of an atomizer 1001 configured as a self-contained unit suitable for combination with a variety of aerosol forming devices, and in relation to FIG. 10*b*, which shows an interior view of the atomizer 1001 with one wall cut away. The atomizer 1001 comprises a chamber 1003 formed of a chamber wall 1005 with an interior surface 1005*a* and an exterior surface 1005*b*. Although the chamber 1003 is illustrated as having a substantially cuboid shape, it is understood that other shapes are encompassed, such as spherical shapes, cylindrical shapes, and the like. The wall 1005 can be a single wall or a plurality of walls and is/are configured to surround the heaters completely—i.e., the heaters are enclosed by the chamber 1003. The interior surface 1005*a* of the wall 1005 can be configured as a black body, as a white body, or neither. The chamber 1003 can include an inlet 1007 whereby air can pass into the chamber and can include an outlet 1009 whereby formed vapor and/or aerosol can pass out of the chamber. The inlet 1007 and outlet 1009 can be sized so as to optimize airflow through the chamber 1003. For example, the inlet 1007 may be larger (i.e., encompass a greater area) than the outlet 1009. If desired, the inlet 1007 and/or the outlet 1009 can include a mesh, screen, or other covering configured to allow passage of gasses therethrough (e.g., air and/or aerosol) while substantially prevent passage of liquid therethrough (e.g., water, aerosol precursor liquid, or the like that may condense within the chamber 1003 or leak from the liquid transport element 1036). A first heater 1033*a* and a second heater 1033*b* are provided within the chamber 1003 in a configuration as otherwise described above with a liquid transport element 1036 positioned between the heaters. The ends 1036*c* and 1036*d* of the liquid transport element 1036 extend through apertures 1011 in the wall 1005 of the chamber 1003. The apertures 1011 can include an element configured to substantially prevent fluid from leaking around the liquid transport element 1036. For example, a gasket 1086 can be included; however, any suitable element that substantially seals the aperture 1011 around the liquid transport element 1036 can be used. As illustrated, the inlet 1007 and outlet 1009 are configured so that an airflow path through the chamber 1003 is substantially parallel with the horizontal axis of the first heater 1033*a* and second heater 1033*b* and/or the horizontal axis of the liquid transport element 1036. The airflow path may be in substantially the same plane as the heaters and/or the liquid transport element. Alternatively, one or both of the inlet and the outlet can be positioned off-axis relative to the horizontal axis of the heaters and/or the liquid transport element. For example, one or both of the inlet and outlet may be substantially perpendicular to the longitudinal axis of the heaters and/or the liquid transport element.

Exemplary embodiments relating to an atomizer positioned within an aerosol forming device are described in relation to FIG. 11. Therein, a cartridge 1104 is formed of a housing 1103 with a base 1140 configured for attaching the cartridge to a control body (see, e.g., control body 102 in FIG. 1). Within the cartridge housing 1103 is a reservoir 1144 that, in the illustrated embodiment, is a fibrous mat that substantially encircles the interior of the cartridge housing and has an aerosol precursor liquid stored therein. A flow tube 1113 is substantially centered along the central, longitudinal axis of the cartridge 1104 and is open at both ends to allow air to flow therethrough. The cartridge 1104 has a mouthend 1127 that includes a mouth opening 1128. An atomizer 1101 is positioned adjacent an end of the flow tube 1113 so that air flowing through the flow tube passes substantially directly into the chamber 1103, which includes a first heater 1133*a* and a second heater (no visible) with a liquid transport element 1136 positioned between the heaters. The ends of the liquid transport element 1136 extend through apertures (see element 1011 of FIG. 10*a*) and make contact with the reservoir 1144. As illustrated, the heaters and the liquid transport element are substantially aligned along the longitudinal axis of the cartridge, and an air path 1192 through the cartridge passes through the projection 1141 in the base 1140, passes through the flow tube 1113, enters the chamber 1103 through the inlet 1107, passes at least in part between the heaters, exits the chamber through the outlet 1109, and passes out of the mouthend 1127 of the cartridge through the mouth opening 1128.

Exemplary embodiments relating to an atomizer positioned within an aerosol forming device are described in relation to FIG. 12. Therein, a tank-style cartridge 1204 is formed of a housing 1203 with a base 1240 configured for attaching the cartridge to a control body. The housing 1203 includes a partition wall 1288 that separates a reservoir 1244, which is an open tank, and a vapor-forming chamber 1201. Within the vapor-forming chamber 1201 is a first heater 1233*a* in a substantially parallel arrangement with a second heater 1233*b*, the two being spaced apart with a liquid transport element 1236 positioned therebetween. The liquid transport element 1236 extends beyond the ends of the heaters, and connecting wicks 1237 are in fluid connection with the liquid transport element and the reservoir 1244. A flow tube 1213 opens through the partition wall 1288 and a mouthend 1227 of the cartridge 1204. A mouthpiece 1223 is connected to the mouthend 1227 of the cartridge 1204 and is substantially open to allow aerosol to pass from the cartridge to a user. An aerosol precursor liquid 1245 is stored in the reservoir 1244 and passes along the connecting wicks 1237 to the liquid transport element 1236 for heating by the first heater 1233*a* and the second heater 1233*b* (such as by radiant heating) to form vapor. Air enters the base 1240, passes through the projection 1241, and mixes with vapor in the vapor-forming chamber 1201 to form an aerosol, which passes through the flow tube 1213 to the mouthpiece 1223 and out the mouth opening 1228. Although the connecting wicks 1237 and the liquid transport element 1236 are illustrated as separate elements, it is understood that they may together form a single liquid transport element. Further, the heaters are illustrated as being substantially perpendicular to the flow of air through the cartridge, but it is understood that the heaters may be arranged in any configuration within the vapor-forming chamber. Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An atomizer for an aerosol delivery device, the atomizer comprising:
    a first heater having a heating surface;
    a second heater having a heating surface; and
    a liquid transport element;
    wherein the first heater and the second heater are spaced apart with the respective heating surfaces facing each other and aligned in a substantially parallel arrangement with the fluid transport element positioned therebetween and not in direct contact with either of the first heater and the second heater such that the heating surface of the first heater and the heating surface of the second heater are each in a direct radiant heating relationship with the liquid transport element; and
    wherein the liquid transport element is substantially flattened having a top surface and a bottom surface and is positioned so as to form a heating space between the top surface of the substantially flattened liquid transport element and the heating surface of the first heater and to form a heating space between the bottom surface of the substantially flattened liquid transport element and the heating surface of the second heater.

2. The atomizer of claim 1, wherein the first heater and the second heater are substantially flattened.

3. The atomizer of claim 1, wherein the first heater and the second heater each comprise a substrate with a heating trace on a surface so as to define the heating surface.

4. The atomizer of claim 3, wherein the heating surface of each of the first heater and the second heater further comprises a passivating layer over the heater trace.

5. The atomizer of claim 1, wherein the liquid transport element comprises a material containing an open pore network.

6. The atomizer of claim 1, wherein the liquid transport element comprises opposing ends, and at least one of the opposing ends of the liquid transport element extends so as to not be in a heating arrangement with the first heater and the second heater.

7. The atomizer of claim 1, further comprising an atomizer housing formed of at least one wall enclosing the first heater element and the second heater element.

8. The atomizer of claim 7, wherein the atomizer housing comprises at least one aperture through which the liquid transport element extends.

9. The atomizer of claim 8, wherein the atomizer housing includes a leak resistive gasket at the at least one aperture.

10. The atomizer of claim 8, wherein the atomizer housing comprises an air inlet and an aerosol outlet.

11. An aerosol delivery device comprising:
    a housing having a mouthend;
    a mouthpiece at the mouthend of the housing
    an aerosol precursor liquid;
    a first heater having a heating surface;
    a second heater having a heating surface; and
    a liquid transport element having at least one end in a wicking arrangement with the aerosol precursor liquid;
    wherein the first heater and the second heater are aligned in a substantially parallel arrangement with a portion of the fluid transport element positioned therebetween such that the heating surface of the first heater and the heating surface of the second heater are each in a direct radiant heating relationship with the liquid transport element; and
    wherein the device includes and airflow path through the housing, said airflow path extending through a space defined between the first heater and the second heater and to the mouthpiece at the mouthend of the housing.

12. The aerosol delivery device of claim 11, wherein the aerosol precursor liquid is physically separated from the first heater and the second heater by at least one wall.

13. The aerosol delivery device of claim 12, wherein the at least one wall at least partially defines a chamber storing the aerosol precursor liquid.

14. The aerosol delivery device of claim 13, wherein the chamber storing the aerosol precursor liquid is substantially annularly arranged relative to the housing.

15. The aerosol delivery device of claim 13, wherein the chamber storing the aerosol precursor liquid is refillable.

16. The aerosol delivery device of claim 12, wherein the at least one wall physically separating the aerosol precursor liquid from the first heater and the second heater includes at least one aperture through which the at least one end of the liquid transport element extends.

17. The aerosol delivery device of claim 16, wherein the at least one aperture includes a leak resistive gasket.

18. The aerosol delivery device of claim 11, wherein the first heater and the second heater are arranged apart so as to define an aerosol forming space therebetween.

19. The aerosol delivery device of claim 18, wherein the first heater and the second heater are arranged such that the aerosol forming space is substantially parallel to a longitudinal axis of the housing.

20. The aerosol delivery device of claim 11, wherein the device further comprises one or more of a controller, a power source, and a flow sensor.

21. The aerosol delivery device of claim 20, wherein the device further comprises a second housing that is connectable with the housing, and wherein one or more of the controller, power source, and flow sensor is positioned in the second housing.

22. A method of forming a vapor for inhalation, the method comprising:
    supplying an aerosol precursor liquid along a liquid transport element that is substantially flattened having a top surface and a bottom surface, a portion of the liquid transport element being positioned between a heating surface of a first heater and a heating surface of a second heater that are aligned in a substantially parallel arrangement such that the heating surface of the first heater and the heating surface of the second heater are each in a direct radiant heating relationship with the liquid transport element; and
    providing power to the first heating element and the second heating element sufficient to cause the first heater and the second heater to heat and vaporize at least a portion of the aerosol precursor liquid supplied along the liquid transport element by direct radiant heating; and
    wherein the first heater and the second heater are spaced apart so as to define an aerosolization space therebetween, the liquid transport element being positioned within the aerosolization space, and wherein the liquid transport element is not in physical contact with either of the first heater and the second heater.

23. The method of claim 22, wherein heating of the aerosol precursor liquid supplied along the liquid transport element is substantially only by radiant heating from the first heater and the second heater.

\* \* \* \* \*